(12) United States Patent
Melvin

(10) Patent No.: US 7,753,837 B2
(45) Date of Patent: Jul. 13, 2010

(54) POWER SYSTEM FOR A HEART ACTUATION DEVICE

(75) Inventor: David Boyd Melvin, Loveland, OH (US)

(73) Assignee: The University of Cincinnati, Cincinnati, OH (US)

(*) Notice: Subject to any disclaimer, the term of this patent is extended or adjusted under 35 U.S.C. 154(b) by 1161 days.

(21) Appl. No.: 11/298,423

(22) Filed: Dec. 8, 2005

(65) Prior Publication Data

US 2006/0155159 A1 Jul. 13, 2006

Related U.S. Application Data

(63) Continuation of application No. PCT/US2004/018318, filed on Jun. 9, 2004.

(60) Provisional application No. 60/477,079, filed on Jun. 9, 2003.

(51) Int. Cl.
*A61M 1/10* (2006.01)
(52) U.S. Cl. .................................................. 600/16
(58) Field of Classification Search .................. 600/16; 623/3.1, 3.15
See application file for complete search history.

(56) References Cited

U.S. PATENT DOCUMENTS

| | | | |
|---|---|---|---|
| 2,826,193 | A | 3/1958 | Arthur |
| 3,053,249 | A | 9/1962 | Smith |
| 3,176,316 | A | 4/1965 | Bodell |
| 3,455,298 | A | 7/1969 | Anstadt |
| 3,513,836 | A | 5/1970 | Sausse |
| 3,590,815 | A | 7/1971 | Shiff |

(Continued)

FOREIGN PATENT DOCUMENTS

EP 0119357 3/1987

(Continued)

OTHER PUBLICATIONS

Melvin, D.V.; Conkle, D; Roberts, A; Stinson, E; "Cardiac Perforamnce and Myocardial Contractility After Experimental Mechanical Ventricular Assistance", J. Thoracic and Cardiovascular Surgery vol. 65, Nol. 6, Jun. 1973. (pp. 876-881).

(Continued)

*Primary Examiner*—Kennedy J Schaetzle
(74) *Attorney, Agent, or Firm*—Wood, Heeon & Evans, LLP

(57) ABSTRACT

Actuator mechanisms on the heart are of several types. In preferred embodiments, they are generally simple, durable, mechanical assemblies and are driven by power delivered from a remote location, generally outside the chest, by a variety of mechanisms. The invention teaches physical mechanisms (1) for transfer of cyclic power from outside the chest to the region of the heart for that purpose, either as translational or rotary motion. Also taught are electromechanical converting mechanisms suitable for delivering power to those transfer devices. The embodiments described herein for either transmission of energy from a site of generation to a conduit (2, 10, 22), and of conduits that then deliver energy to heart actuators, have contours and interfaces designed to promote a favorable biologic response similar to the pseudosynovial capsules that surround artificial joints. Further, design features are chosen to avoid both non-vented gas-filled chambers and static collections of tissue fluid.

22 Claims, 14 Drawing Sheets

U.S. PATENT DOCUMENTS

| | | | |
|---|---|---|---|
| 3,595,230 A | 7/1971 | Suyeoka et al. |
| 3,613,672 A | 10/1971 | Schiff |
| 3,668,708 A | 6/1972 | Tindal |
| 3,713,439 A | 1/1973 | Cabezudo et al. |
| 3,725,984 A | 4/1973 | Graber |
| 3,791,388 A | 2/1974 | Rosen et al. |
| 3,827,426 A | 8/1974 | Page et al. |
| 3,835,864 A | 9/1974 | Rasor et al. |
| 3,983,863 A | 10/1976 | Janke et al. |
| 4,149,277 A | 4/1979 | Bokros |
| 4,187,558 A | 2/1980 | Dahlen et al. |
| 4,192,293 A | 3/1980 | Asrican |
| 4,255,820 A | 3/1981 | Rothermel et al. |
| 4,345,601 A | 8/1982 | Fukuda |
| 4,453,537 A | 6/1984 | Spitzer |
| 4,519,392 A | 5/1985 | Lingua |
| 4,536,893 A | 8/1985 | Parravicini |
| 4,585,458 A | 4/1986 | Kurland |
| 4,597,766 A | 7/1986 | Hilal et al. |
| 4,621,617 A | 11/1986 | Sharma |
| 4,690,134 A | 9/1987 | Snyders |
| 4,713,075 A | 12/1987 | Kurland |
| 4,773,910 A | 9/1988 | Chen et al. |
| 4,809,676 A | 3/1989 | Freeman |
| 4,846,831 A | 7/1989 | Skillin |
| 4,904,255 A | 2/1990 | Chareire et al. |
| 4,917,700 A | 4/1990 | Aikins |
| 4,936,857 A | 6/1990 | Kulik |
| 4,946,377 A | 8/1990 | Kovach |
| 4,957,477 A | 9/1990 | Lundback |
| 4,964,414 A | 10/1990 | Handa et al. |
| 5,013,304 A | 5/1991 | Russell et al. |
| 5,049,155 A | 9/1991 | Bruchman et al. |
| 5,061,283 A | 10/1991 | Silvestrini |
| 5,109,843 A | 5/1992 | Melvin et al. |
| 5,116,372 A | 5/1992 | Laboureau |
| 5,119,804 A | 6/1992 | Anstadt |
| 5,131,905 A | 7/1992 | Grooters |
| 5,139,517 A | 8/1992 | Corral |
| 5,169,381 A | 12/1992 | Snyders |
| 5,192,314 A | 3/1993 | Daskalakis |
| 5,197,983 A | 3/1993 | Berman et al. |
| 5,201,880 A | 4/1993 | Wright et al. |
| 5,217,495 A | 6/1993 | Kaplan et al. |
| 5,256,132 A | 10/1993 | Snyders |
| 5,258,021 A | 11/1993 | Duran |
| 5,334,217 A | 8/1994 | Das |
| 5,345,949 A | 9/1994 | Shlain |
| 5,358,519 A | 10/1994 | Grandjean |
| 5,366,459 A | 11/1994 | Yoon |
| 5,370,685 A | 12/1994 | Stevens |
| 5,383,840 A * | 1/1995 | Heilman et al. ............... 600/17 |
| 5,385,528 A | 1/1995 | Wilk |
| 5,409,499 A | 4/1995 | Yi |
| 5,411,481 A | 5/1995 | Allen et al. |
| 5,417,683 A | 5/1995 | Shiao |
| 5,443,504 A | 8/1995 | Hill |
| 5,456,715 A | 10/1995 | Liotta |
| 5,484,391 A | 1/1996 | Buckman et al. |
| 5,487,760 A | 1/1996 | Villafana |
| 5,533,958 A | 7/1996 | Wilk |
| 5,540,705 A | 7/1996 | Meade et al. |
| 5,571,176 A | 11/1996 | Taheri |
| 5,584,840 A | 12/1996 | Ramsey et al. |
| 5,593,424 A | 1/1997 | Northrup, III |
| 5,620,452 A | 4/1997 | Yoon |
| 5,643,308 A | 7/1997 | Markman |
| 5,655,548 A | 8/1997 | Nelson et al. |
| 5,667,526 A | 9/1997 | Levin |
| 5,697,978 A | 12/1997 | Sgro |
| 5,702,343 A | 12/1997 | Alferness |
| 5,709,695 A | 1/1998 | Northrup |
| 5,713,954 A | 2/1998 | Rosenberg et al. |
| 5,738,626 A | 4/1998 | Jarvik |
| 5,738,627 A | 4/1998 | Kovacs et al. |
| 5,749,883 A | 5/1998 | Halpern |
| 5,766,250 A | 6/1998 | Chervitz et al. |
| 5,797,932 A | 8/1998 | Min et al. |
| 5,800,528 A | 9/1998 | Lederman et al. |
| 5,824,071 A | 10/1998 | Nelson et al. |
| 5,846,255 A | 12/1998 | Casey |
| 5,849,019 A | 12/1998 | Yoon |
| 5,910,124 A | 6/1999 | Rubin |
| 5,957,977 A | 9/1999 | Melvin |
| 5,961,440 A | 10/1999 | Schweich et al. |
| 5,981,827 A | 11/1999 | Devlin et al. |
| 6,019,722 A | 2/2000 | Spence et al. |
| 6,045,497 A | 4/2000 | Schweich et al. |
| 6,050,936 A | 4/2000 | Schweich et al. |
| 6,059,715 A | 5/2000 | Schweich et al. |
| 6,077,214 A | 6/2000 | Mortier et al. |
| 6,085,754 A | 7/2000 | Alferness et al. |
| 6,110,100 A | 8/2000 | Talpade |
| 6,123,662 A | 9/2000 | Alferness et al. |
| 6,125,852 A | 10/2000 | Stevens et al. |
| 6,159,224 A | 12/2000 | Yoon |
| 6,162,168 A | 12/2000 | Schweich et al. |
| 6,165,119 A | 12/2000 | Schweich et al. |
| 6,165,120 A | 12/2000 | Schweich et al. |
| 6,165,186 A | 12/2000 | Fogarty et al. |
| 6,170,415 B1 | 1/2001 | Inoue et al. |
| 6,179,791 B1 | 1/2001 | Krueger |
| 6,183,411 B1 | 2/2001 | Mortier et al. |
| 6,214,047 B1 | 4/2001 | Melvin |
| 6,221,103 B1 | 4/2001 | Melvin |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,293,906 B1 | 9/2001 | Vanden Hoek et al. |
| 6,299,621 B1 | 10/2001 | Fogarty et al. |
| 6,312,445 B1 | 11/2001 | Fogarty et al. |
| 6,319,231 B1 | 11/2001 | Andrulitis |
| 6,324,430 B1 | 11/2001 | Zarinetchi et al. |
| 6,324,431 B1 | 11/2001 | Zarinetchi et al. |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,402,680 B2 | 6/2002 | Mortier et al. |
| 6,464,655 B1 * | 10/2002 | Shahinpoor ............... 601/153 |
| 6,592,619 B2 | 7/2003 | Melvin |
| 7,081,084 B2 | 7/2006 | Melvin |
| 2002/0007216 A1 * | 1/2002 | Melvin ............... 623/3.11 |
| 2003/0023132 A1 | 1/2003 | Melvin |

FOREIGN PATENT DOCUMENTS

| | | |
|---|---|---|
| EP | 0583012 | 7/1996 |
| WO | WO98/29041 | 7/1998 |
| WO | WO99/30647 | 6/1999 |
| WO | WO99/53977 | 10/1999 |
| WO | WO0002500 | 1/2000 |
| WO | WO0006026 | 2/2000 |
| WO | WO0006028 | 2/2000 |
| WO | WO0016700 | 3/2000 |
| WO | WO0018320 | 4/2000 |
| WO | WO0047270 | 8/2000 |
| WO | WO0167985 | 2/2001 |
| WO | WO0128455 | 4/2001 |
| WO | WO0185061 | 11/2001 |
| WO | WO0191667 | 12/2001 |
| WO | WO0195830 | 12/2001 |
| WO | WO0195831 | 12/2001 |

| | | |
|---|---|---|
| WO | WO0195832 | 12/2001 |

OTHER PUBLICATIONS

Melvin, D.B., "Cardiovascular Surgery: Myocardial Preservation, Cardiorespiratory Support I", American Heart Assoc. Abstract, Circulation Part II, vol. 68, No. 4; Scientific Sessions for Nurses; 37th Ann. Meeting; Nov. 14-17, 1983. (1 Page).

Melvin, D.; Schima, H.; Losert, U.; Wolner, E., "Long-Term Ventricular Wall Actuation: Can and Should it be Systematically Explored?", Artificial Organs, vol. 20, No. 1, 1996. (pp. 63-68).

Melvin, D.B., et al., "A Physical Analog of the Failing Left Ventricle for In Vitro Studies of Mechanical Wall Actuation", Artificial Organs, vol. 20, No. 3, 1996. (pp. 227-239).

Melvin, D.B., et al., "Reduction of Ventricular Wall Tensile Stress by Geometric Remodeling Device", ASAIO Journal (Abstract), vol. 45, No. 2 p. 166, Mar. 17, 1999. (1 page).

Melvin, D.B., "Device-Induced Ventricular Geometric Remodeling: Appraisal of Critical Issues", J. of Cardiac Surgery (Accepted for publication), Presented at the 3rd Symposium of the Soc. of Cardiac Volume Reduction, Apr. 9, 2000 in Osaka, Japan.

Two-page International Search Report for PCT/US2003/022055, mailed May 11, 2004.

Farrar, et al. (1992), "A New Skeletal Linear-pull Energy Convertor as a Power Source for Prosthetic Circulatory Support Devices", Journal of Heart and Lung Transplantation, pp. S341-S349.

Farrar, et al. (1995), "Mechanical Advantage of Skeletal Muscle as a Cardiac Assist Power Sources", ASAIO Journal, pp. M481-M484.

Sasaki, et al. (1992), "A Skeletal Muscle Actuator for an Artificial Heart", ASAIO Journal, pp. M507-M511.

Acker, et al. (1987), "Skeletal Muscle as the Potential Power Source for a Cardiovascular Pump; Assessment in Vivo Science", Science, vol. 236, pp. 324-327.

Salmons, et al. (1992), "Cardiac Assistance From Skeletal Muscle: A Critical Appraisal of the Various Approaches", British Heart Journal, vol. 68, pp. 333-338.

Ugolini (1986), "Skeletal Muscle for Artificial Heart Drive: Theory and in Vivo Experiments", Biomechanical Cardiac Assist, pp. 193-211.

Reichenbach, et al. (1997), "In Vivo Studies of an Implantable Energy Convertor for Skeletal Muscle Powered Cardiac Assist", ASAIO Journal, vol. 43, pp. M668-M672 (and Abstract).

Geddes, et al. (1991), "Power Capability of Skeletal Muscle to Pump Blood", Trans Am Soc. Artif. Intern Organs, vol. XXXVII, pp. 19-23.

Reichenbach, et al. (1992), "Characterization and Work Optimization of Skeletal Muscle as a VAD Power Source", ASAIO Journal, pp. M359-M363.

Melvin, et al. (1997), "Coupling of Skeletal Muscle to a Prosthesis for Circulatory Support", ASAIO Journal, vol. 43, pp. M434-M441.

\* cited by examiner

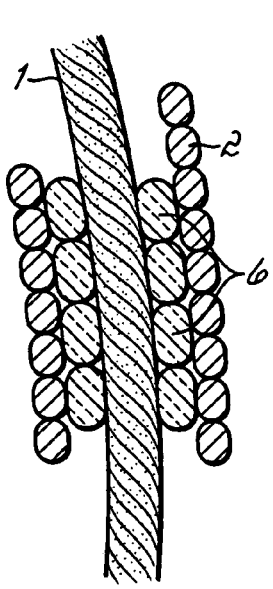
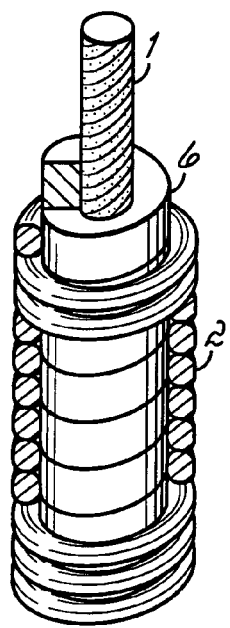
FIG. 4a
FIG. 4b
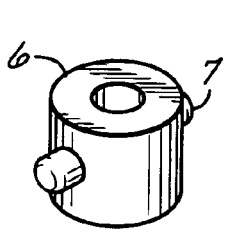
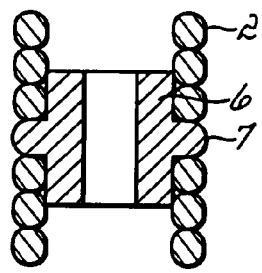
FIG. 4c
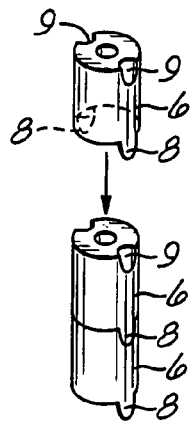
FIG. 4d

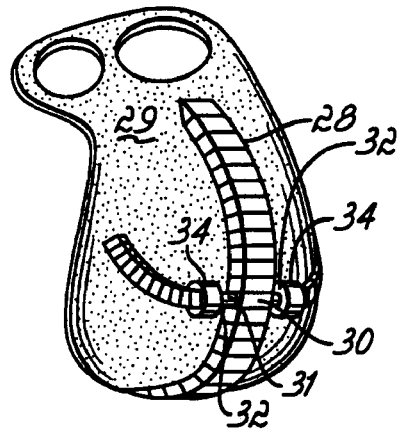
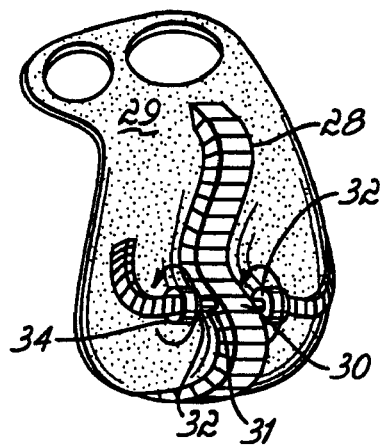
FIG. 15a          FIG. 15b
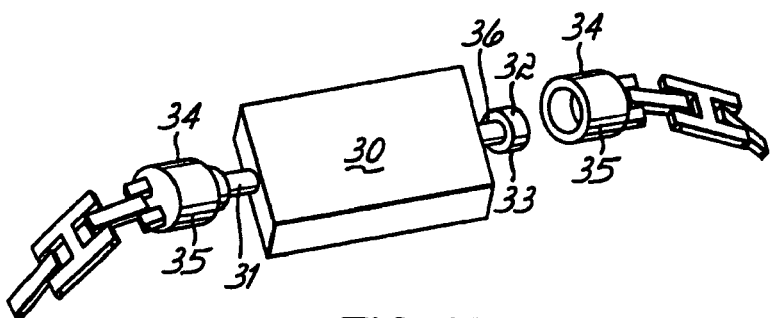
FIG. 15c
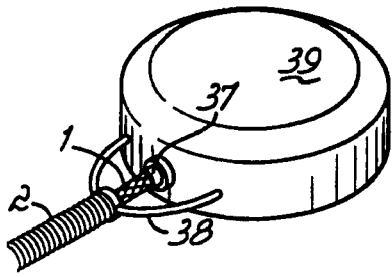
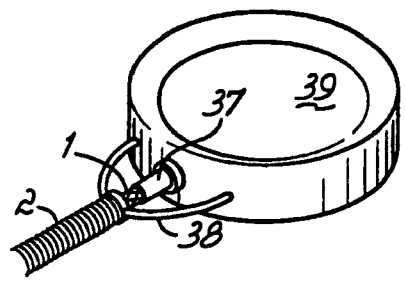
FIG. 16a          FIG. 16b
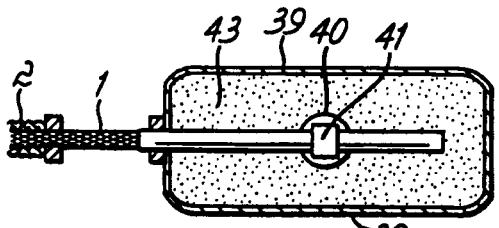
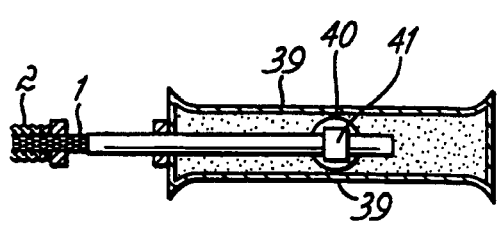
FIG. 16c          FIG. 16d

POWER SYSTEM FOR A HEART ACTUATION DEVICE

This application is a continuation of PCT/US2004/018318 filed on Jun. 9, 2004, which claims priority of U.S. Provisional Patent Application No. 60/477,079, filed Jun. 9, 2003. The disclosure of each priority application is hereby incorporated by reference herein in its entirety.

FIELD OF THE INVENTION

This invention relates generally to assisting the natural heart in operation and, more specifically, to components to assist in actuating one or more walls of the natural heart.

BACKGROUND OF THE INVENTION

The human circulatory system is critical for survival and systematically provides nutrients and oxygen as well as removing harmful waste products from all parts of the body. The heart is a critical component of the circulatory system in that it provides pumping power. Generally the right side of the heart receives blood from the 'systemic circulation' (all the body except the lungs) and pumps it into the 'pulmonary circulation' (lungs), whereas the left side of the heart receives blood from the lungs and pumps it back into the systemic circulation. Each side comprises an inflow or collecting chamber with a thin muscular wall, its 'atrium' and a thicker, more powerful muscular pumping chamber, its 'ventricle', which alters volume cyclically due to contraction and relaxation of the muscles in its walls. One-way valves are positioned in the passageway between the left and right atrium and the corresponding ventricle, and between each ventricle and the large arteries, which conduct blood into the systemic or pulmonary circulation, respectively. Because of this arrangement, each atrium may gently contract, causing blood to flow across the 'atrioventricular' valve into the ventricle, with that valve then closing to prevent return. Similarly, each ventricle may then forcefully contract, causing blood to flow across the outflow valves into the systemic or pulmonary circulation. A physical ailment or condition which compromises the effective muscular contraction in the walls of one or more chambers of the heart can therefore be particularly critical and may result in a condition which must be medically remedied if the person is to long survive.

More specifically, the muscle of the heart may degrade for various reasons to a point where the heart can no longer provide sufficient circulation of blood to maintain the health of a person at an acceptable level. In fact, the heart may degrade to the point of failure and not been able to sustain life. To address the problem of a failing natural heart, solutions are offered to maintain the circulation. Some of these solutions involve replacing the heart. Some involve assisting it with mechanical devices. Some are directed to maintain operation of the existing heart.

The heart may be removed and replaced with either a mechanical device (a total artificial heart) or a natural heart from another human or an animal (heart transplant). Artificial heart use has been complicated by consequences of blood clots forming on the internal lining. The most serious consequence is a breaking loose of such clots, which are then propelled into various parts of the circulation. In the event of such a clot being propelled into the brain, a disabling or fatal stroke may result. While human heart transplantation is limited by rejection, a response of the body's immune system, this may usually be controlled by medications to the degree that half of all recipients survive at least 10 years, generally with acceptable health and function. However a more serious limitation is numbers of available donors. These are usually accidental death victims whose hearts maintain function despite brain death. Currently these are available for less than 1 to 2 percent of potential beneficiaries (about 2000 per year in the United States for over 200,000 people dying of heart failure annually in the same country, for example).

Mechanical auxiliary pumps may assist the heart. These are of three general types: counterpulsators, pulsatile assist systems, and nonpulsatile assist systems. Counterpulsators such as intraaortic balloon pump cyclically remove or displace blood from the arterial system in synchrony with the natural heart's beat and, without valves, may perform substantial work for a weakened heart. Pulsatile assist systems (ventricular assist devices) are similar to artificial hearts except that they are used in addition to one or both sides of the heart rather than instead of the heart. They receive blood from either the atrium or ventricle on one side of the circulation and pump it into that side's arterial system, relieving the ventricle of part of its volume load, pressure load, or both. They consist of a blood chamber with at least partial wall flexibility, inflow and outflow valves, and some means, usually pneumatic, hydraulic, or electric, by which the wall may be moved and volume altered to pump blood. Nonpulsatile assist systems are rotary pumps, either centrifugal, axial flow, or a combination, that similarly pump blood in a steady flow from atrium or ventricle into circulatory systems. All of these mechanical pumps have extensive non-living material surfaces that contact blood. The complications of blood clotting with stroke or other serious aftermaths described with artificial hearts also occur with these mechanical auxiliary pumps.

Because of the severe shortage of human donor hearts for transplant, unsolved immunologic problems of animal donor hearts for transplants and prevalence of serious complications of artificial blood-contacting surfaces of both artificial hearts and auxiliary pumps, means of aiding the actuation of the natural heart walls have been attempted. Both skeletal muscle wraps ('cardiomyoplasty') and mechanical compression devices ('mechanical ventricular actuation') have been used. In either approach, the external wall surfaces of the heart are compressed and the heart volume altered, thereby pumping blood out of the chambers. Muscle wraps are limited by available space relative to muscle mass required for power, as well as by intrinsic stiffness that compromises re-filling between beats. Both muscle wraps and mechanical compression devices are limited by inability to effectively restrict volume and pressure delivery to one chamber of the heart. This chamber restriction is important because the two sides of the circulation require far different pressures for acceptable function (usually the systemic pressure is 3 to 5 times as high as is the pulmonary pressure). Compressive patterns of either muscle wraps or mechanical devices may also distort heart valves, which can lead to valve leakage.

Therefore, to be effective and safe, mechanical pumping of a person's existing heart, such as through mechanical compression of the ventricles or some other action thereon, must address these issues and concerns in order to effectively and safely pump blood. Specifically, the weakened ventricle or ventricles must rapidly and passively refill between beats at low physiologic pressures, and the valve function must be physiologically adequately. The blood flow to the heart muscle must not be impaired by the mechanical device. Still further, the left and right ventricular pressure independence must be maintained within the heart.

Internal stabilizing components to complete the three-dimensional control of a chambers' boundaries, which components are suspended through the substance of heart walls from the external (to the heart) actuating mechanism should be a useful adjunct. These provide a means to facilitate the precise control of actuation—determining the prescribed pattern and distribution needed to (1) prevent valvular distortion, (2) avoid myocardial blood flow compromise, (3) provide a type of shape alteration of the actuated chamber at end-actuation which will facilitate passive refilling during shape restoration, and (4) ensure relative independence of pressure in the various chambers.

Specifically, U.S. Pat. No. 5,957,977, which is incorporated herein by reference in its entirety, discloses an actuation system for the natural heart utilizing internal and external support structures. That patents provides an internal and external framework mounted internally and externally with respect to the natural heart, and an actuator device or activator mounted to the framework for providing cyclical forces to deform one or more walls of the heart, such as the left ventricular free wall. The invention of U.S. patent application Ser. No. 09/850,554, which has issued as U.S. Pat. No. 6,592,619 further adds to the art of U.S. Pat. No. 5,957,977 and that patent is also incorporated herein by reference in its entirety. The application specifically sets forth various embodiments of activator or actuator devices, which are suitable for deforming the heart walls and supplementing and/or providing the pumping function for the natural heart.

While the actuation systems of those patents provide a desirable actuation of the natural heart, it is further desirable to improve upon delivery of mechanical power to those actuation systems. It is particularly desirable to provide power delivery in ways that minimize risk of either mechanical or biologic malfunction over an extremely large number of cycles. The natural heart beats approximately 1 billion times ($10^9$ cycles) over 25 years, a reasonably desirable endurance for middle-aged recipients of such devices.

Several obstacles to reaching that goal have been observed in earlier and in conventional implanted medical devices, both for cardiovascular and other purpose.

First, devices in which action of mechanical members requires a residual air chamber (for example, many of the electrical ventricular assist devices) have only succeeded, clinically or experimentally, by having either an external vent or a frequently refillable compliance chamber.

Second, prolonged cyclic stress on flexing polymer membranes has often been complicated by either membrane mechanical failure or mineralization with unacceptable stiffening.

Third, crevasses and spaces between mechanical members, which do not allow and promote free flow of tissue fluid, are followed by several complications of such stasis. Infection is particularly common due to restricted access to such areas by the immune system. Interfaces between metals under such conditions are susceptible to fretting corrosions. With or without fluid stasis, interfaces between two or more dissimilar metals may generate galvanic currents with electrolytic corrosion of one or both metals.

Fourth, irregular moving surfaces and edges may mechanically damage surrounding tissue or encourage immobilizing scar tissue that inhibits function.

Fifth, mechanical linkages used in machinery typically deliver energy at very near the rate and cycle at which it is received. The heart's ejection time, and thus the rate of energy delivery required, however, varies with blood pressure and other physiological changes. Excessive blood pressure spikes are risked by linkages not permitting transient energy storage.

The embodiments described herein are based on avoidance of these complications and so facilitate prolonged clinical durability with minimization of biologic and mechanical failure risk both in (1) transfer of mechanical energy from an extrathoracic source into the chest, and in (2) electromechanical energy conversion. Specifically, it is a common characteristic of most of the embodiments described herein for either transmission of energy from a site to generation to a conduit, and of conduits that then deliver energy to heart actuators, that contours and interfaces are designed to promote a favorable biologic response similar to the pseudosynovial capsules that surround artificial joints.

BRIEF DESCRIPTION OF THE DRAWINGS

FIG. 4 is a helical compression conduit in which torroidal or cylindrical bearings of ceramic or other material to separate central cable and sheath so as to avoid metal-on-metal friction.

FIG. 15 shows a system of embedded solenoids, which may be configured for inducing rotation of at least one region of a heart wall actuator.

FIG. 16 is a mechanism by which energy may be transferred from a fluid-filled electromechanical converter by physical couplings, which slide back and forth, or rotate back and forth within a port of socket in the housing wall, with slight flexibility of at least one wall of the converter housing for cyclic volume compensation.

PART NUMBERS

Figure 1A:
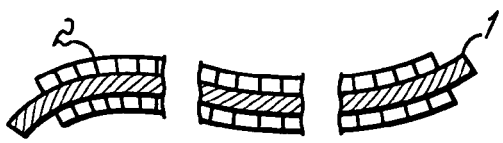
FIG. 1 *a-c* is a conventional coiled (helical) compression conduit for a traction tether of the type frequently used in mechanical devices.
FIG. 1*d* illustrates a basic system for use of the embodiments of the present invention to transfer power from a power source, such as outside a body, to an actuator proximate the heart.
Figure 1B:
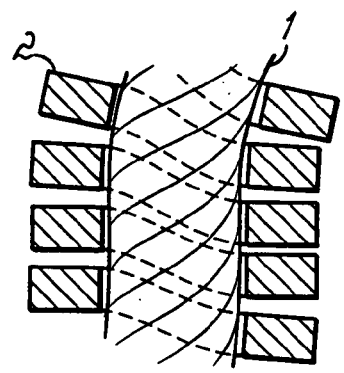
Figure 1C:
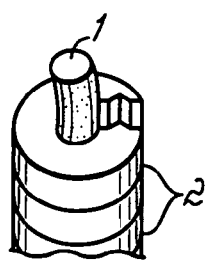

1. Traction tether
2. Helical compression sheath
3. Interhelical fenestration for fluid passage
4. Energy-storing segment to be interposed in a compression conduit
5. Compression spring in the energy storing segment
6. Cylindrical bearings in compression sheath
7. Radial anti-translation projection on cylindrical bearing
8. Longitudinal anti-rotation projection on cylindrical bearing
9. Longitudinal anti-rotation socket in cylindrical bearing
10. Independent torroidal compression bead
11. Channel in independent bead for tether
12. Absorbable mesh for temporary stabilization of beads
13. Absorbable adhesive for temporary stabilization of beads
14. Thicker side of an asymmetrical independent compression bead
15. Thinner side of an asymmetrical independent compression bead
16. Relatively straight sequence in a stack of compression beads
17. Concave curvature of a stack of compression beads
18. Rigid tube segment to couple a stack-of-beads power conduit
19. Interruption in circumference of a compression bead
20. Radial groove in a compression bead
21. Interposed compression spring in a stack-of-beads compression conduit
22. Helical conduit for rotary power
23. Driving end of a helical rotary power conduit
24. Driven end of a helical rotary power conduit
25. Compression-resisting core for a helical rotary power conduit
26. Articulating link for a flexible torsion power conduit
27. Pin joining links of an articulating torsion power conduit
28. Train of links heart wall actuator
29. Active cardiac jacket
30. Junctional link
31. Hubs on junctional link
32. North poles of permanent magnets
33. South poles of permanent magnets
34. Solenoid-equipped socket
35. Conductor leads
36. Deformable spring coupling
37. Shaft
38. Strut to support shaft
39. Flexible regions of housing
40. Motor
41. Cam or gear mechanism
42. Flexible region such as a bellows in housing
43. Lubricating fluid
44. Solenoid in sliding linear electromechanical converter
45. Housing for solenoid in linear electromechanical converter
46. Permanent magnet in linear electromechanical converter
47. Housing for permanent magnet in linear electromechanical converter
48. Electric lead wires
49. Solenoid windings
50. Fixation flanges or tabs
51. Fixation bands
52. Solenoid in rotary electromechanical converter
53. Housing for solenoid in rotary electromechanical converter
54. Cylindrical channel for armature in electromechanical converter
55. Windings for field solenoids rotary electromechanical converter
56. Electric lead wires to rotary electromechanical converter
57. Cylindrical armature for rotary electromechanical converter
58. Permanent magnets in armature
59. Armature housing
60. Flexible shaft(s) for rotary electromechanical converter
61. Moving permanent magnet in magnetically coupled energy transfer system
62. Shaft for linearly moving permanent magnet
63. Housing for linearly moving permanent magnet
64. Lubricating fluid surrounding moving permanent magnet
65. Housing surface
66. Shaft-mounted, reciprocally rotating permanent magnet positioned centrally
67. Housing for rotating permanent magnet
68. Lubricating liquid 69. Concentric external shell housing reciprocally moving permanent magnet positioned peripherally
70. Field coils for a cable winding motor set directly in tissue
71. High permeability core for field coils of cable winding motor
72. Housing for field coils of cable winding motor
73. Shell for armature of in-tissue cable winding unit
74. Permanent magnets in armature of in-tissue cable winding unit
75. Bracket for traction conduit of cable winding unit
76. Grooved channel in armature for cable or tether as it is wound
77. Solenoids in stacked-solenoid type of direct in-tissue linear electromechanical converter
78. Permanent magnets in stacked-solenoid type of direct in-tissue linear electromechanical converter
79. Bracket mounting compression sheath energy conduit to stacked-solenoid electromechanical converter Power Conduits Power conduits have been designed and methods of placement have been developed in order to transmit power from a source, generally outside the chest, to the actuator or actuators. These are generally one of two types, (A) those intended for conducting translational movement and (B) those intended for conducting rotational movement.

Conduits of Translational Motion

A traction cable conduit (or, synonymously, a traction tether conduit, intended to transmit cable or tether motion for inducing curvature in at least one region of an articulating-link actuator, may be both (a) sufficiently flexible longitudinally, at least in some regions, to neither impede, nor damage tissue in the occurrence of, expected body motions and (b) sufficiently stiff in compression to ensure that cable motion relative to the conduit applied at the power-supply end (generally the outer end) will reliably impose motion of the cable relative to the conduit at the actuator end (generally the inner end). As used here, 'tether' and 'cable' may mean any flexible tension member, with examples being metal cable, polymer rope, monofilaments of any flexible material, chains of any material, and so forth. The principle of operation is that the tether is generally surrounded by the conduit, and energy is delivered to one end (the input end) of the assembly by pulling out some length of tether from the conduit. Except for length loss lost to stretching of tether or compression of conduit, or straightening of the tether within the conduit, an equal length of tether must of necessity move into the other end (the effecter end) of the conduit, with the capacity to do work. Both work consumed at the input end and work done at the effecter end may be computed as the integral of force-times-velocity of tether movement across the range of movement. The work done at the effecter end is necessarily equal to that consumed at the input end minus frictional, inertial, viscoelastic, and other losses.

Conduits based on this principle presently serve well in several nonmedical applications because the quantitative degree of both tensile force and displacement delivered to the cable at its power supply end relative to the conduit exceed the force and displacement recovered at the actuator end only by relatively small amounts of frictional loss and of transiently stored strain-energy.

For the present purpose, a traction cable conduit of this type may have the outer end in the subcutaneous tissue for connection to a power supply and the inner end adjacent the heart for connection to a heart wall actuator or actuators.

To explain background of and purpose for the invention, the conventional traction cable conduits familiar in applications such as throttle cables of gasoline motors and brake cables for bicycles will be briefly reviewed. That brief explanation is followed by a listing of problems risked by these conventional tether compression sheaths should they be subjected to biologic implantation, accompanying each stated problem with the teaching of one or more alternative means to reduce or eliminate it.

Conventional traction tether (or cable) conduits (or 'sheaths') are generally one of two types, with load bearing components generally of fatigue resistant material such as a metal, to allow near one-to-one transmission of force and displacement:

a metal coil [1] of either flat (usual), round or other profile wire that surrounds the tether [2], in which the turns of the coil rest upon each other to provide needed compressive counterforce to tether tension (FIG. 1a, b, c.)

a set of longitudinal wires embedded or enclosed in a polymer matrix, in which the stiffness of the wires provides compressive counterforce (no figure).

Figure 1D:

FIG. 1d shows a basic system for implementing embodiments of the present invention wherein various conduits are used to transfer power from a power source, which might be located outside the body to an actuator that is located inside the body and adjacent to a heart.

At least one of these types of sheaths is associated with the following undesirable effects during long-term biologic implantation, which are addressed by the teachings of this invention:

1. There is limited exchange of fluid that would be trapped inside the conduit, hampering access of cellular immune system for prevention and control of infection.

Figure 2:
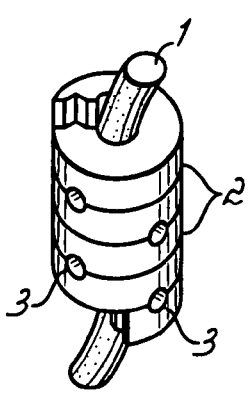
FIG. 2 is an adaptation of such a conduit to relieve fluid stasis when implanted in living tissue by means of vents between helical coils.
Figure 3A:
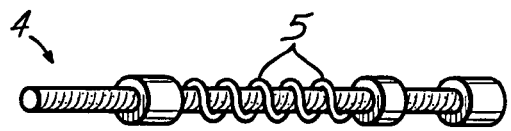
FIG. 3 is an adaptation of a helical compression conduit comprising an interposed compression spring for storage of strain energy to facilitate matching of energy input and dispersion rates.
Figure 3B:
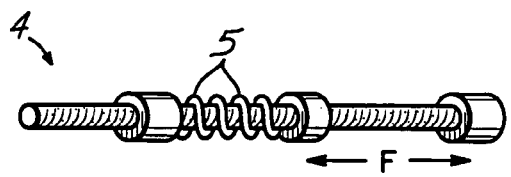
Figure 3C:
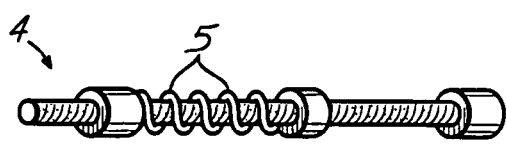
Figure 3D:
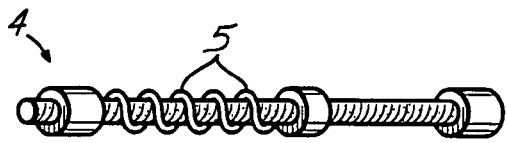
Figure 5A:
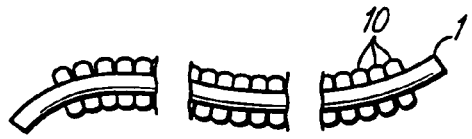
FIG. 5 illustrates a stacked independent bead traction cable conduit that would minimize flexural stiffness of a conventional helical conduit.
Figure 5B:
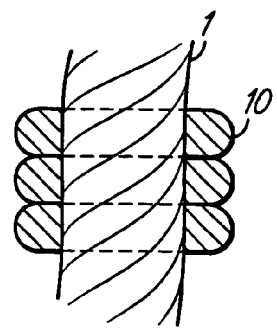
Figure 5C:
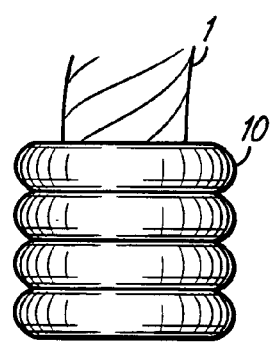
Figure 5D:
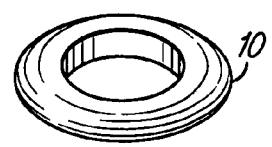

For this purpose, an embodiment shown in FIG. 2 is intended to increase tissue fluid exchange, The traction cable conduit of this type may be constructed grossly similarly to the conventional helix or coil of FIG. 6—with the exception that periodic radial grooves or apertures [3] in at least one of facing turns are provided.

2. Rate of energy output is closely matched to rate of energy input. That is, if the motion of the tether relative to the conduit or sheath at the input end occurs in, for example, 10 milliseconds, so will (with extremely small variance) the relative motion at the output end. It would be of great potential advantage in cardiac device driving applications to uncouple timing so that, for example, a near instantaneous input (e.g., from single solenoid activation) could provide output rate more nearly matched to output impedance.

For this purpose, in another embodiment shown in FIG. 3, a grossly similar traction cable conduit of this type may be constructed of a helix or coil in which at least one segment [4] contains two or more successive coils [5] which are separated when unstressed (i.e., not compressed), so that they may be compressed toward each other during force delivery to increase transient energy storage and allow a more prolonged energy release at the actuator end. This produces a linear energy storage system whose purpose is to mechanically store energy in the form of elastic strain energy in one or more springs. This allows use of a very rapid energy production (e.g., by a solenoid) to drive a slower energy consuming process (e.g., ejection of blood out of a cardiac chamber).

This would allow elastic power storage similar to the effective bar-spring in the Novacor pump (instantly produce an evacuation force that is sustained, dissipating only as the ventricle empties over a period of time dictated by impeding summation of blood inertia, sac stiffness, large vascular elasticity, fine vascular resistance, and so forth). The principle of this feature of the invention is including measurable elastic behavior into the compressive sheath of a cable-in-sheath power transfer mechanism between (a) an electromechanical or muscle-harnessing energy converter/driver on one end and (b) a power-requiring medical device such as a heart wall actuator) on the other. This is achieved by having the tether in a coiled sheath that is deliberately not the typical collapsed-coil, non-compressible (other than incidentally to straightening) construction but actually designed with controlled linear expansibility/collapsibility.

Delivery of power to this storage/transfer device is described below as pulling on the tether (cable, cord, chain, etc.—the tension member inside), elastically compressing the sheath to store energy for later release.

FIG. 3 shows a short segment [4] in which strain energy is stored by compression of the sheath coil [5]. In FIG. 3a, the unit is relaxed. In FIG. 3b, displacing force of the coil relative to the tether [1] has been near-instantly applied to the right end, as could happen with a solenoid driving force—and totally transmitted to elastic strain energy within the metal of the coil. FIG. 3c shows partial, and FIG. 3d complete, re-conversion of the strain energy over time to force-plus-displacement at the left end.

Figure 7:
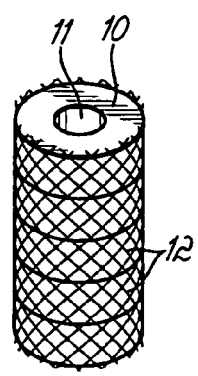
FIG. 7 shows a mesh sheath of absorbable or other material that holds beads of FIG. 5 aligned to facilitate fabrication and implantation.

An added benefit to open-coil sheath of FIG. 3—whether intermittently compressed, extended, or both alternatively—is free flow of bathing tissue fluid within the sheath and between sheath and tether, facilitated by to-fro mechanical action. This avoids the issue in 'A' above: microloculation within the sheath, which would otherwise need addressing by deliberate fenestration to minimize colonization/infection potential, as in the feature of FIG. 7 described above.

There are several obvious variations in devices for linear energy storage. One could optionally reverse the active phase. Instead of (a) pulling on the cable (cord, chain, whatever—the tension member inside), elastically compressing the sheath to store energy for later release, we could (b) push the (now necessarily rather stiff) cable, allowing the sheath to elastically extend in actuation.

If the tether is a metal cable, the repetitive friction of tether in sheath is generally either metal-on-metal or metal-on-soft-polymer, either with limited lubrication, and both with substantial risk of unacceptable wear in the continuing motion and aqueous environment to which power conduits for implanted cardiac devices are subjected. The inner surface of the sheath, which contacts the tether, is typically metal—the coil or wire—or else a flexible and compliant polymer liner. The outer surface of the tether is either metal or a soft compliant polymer covering. The only practical lubricant is typically the naturally occurring tissue fluid, which is a dilute protein in water solution. Wear resistance of the polymer and/or metals is limited in that environment. In metal/polymer interfaces, metals are harder than polymers and tend to erode them. In interfaces between similar metals fretting corrosion is a difficulty. In interfaces between dissimilar metals, galvanic electrolytic corrosion is a difficulty.

For this purpose, in yet another embodiment shown in FIG. 4, a coiled metal traction cable conduit [2] may be lined with cylindrical bearings [6] made of ceramic or other compression resistant, low frictional material, for improved frictional behavior when used with a metal traction cable or tether. These surround the tether [1]. This is intended to reduce tendency to fretting corrosion in the event of similar metals for conduit and cable, or galvanic damage from galvanic currents in the event of dissimilar metals or other materials.

These may be either stacked free as in the sectional view of FIG. 4a and cut-a-way perspective view of FIG. 4b, have one or more features such as radial projections [7] of FIG. 4c which maintain position (generally translationally) relative to the coil, or have one or more features such as the longitudinal projections [8] and slots [9] of FIG. 4d (a single bearing above; two adjacent bearings below), which maintain position (generally rotationally) relative to each other. The latter may be needed to keep an even spatial distribution of bearings, because without it, the radial projections [7] of FIG. 4c would still allow individual bearings to advance or recede relative to one another by a screw-like motion within the coil.

There is no mechanism by which lengths of a conventional simple helical conduit can adjust to a resting curved position other than having persistent gaps between turns all along the convex side of the conduit over any curved region. This will result repetitive elastic and viscoelastic loss of energy. While acceptable in the occasional use as, for example, a bicycle brake driver, the energy loss to hysteresis, as well as the repetitive motion in tissue associated, may be very significant in the continuous cycling of a cardiac device power conduit.

For this purpose, still another feature of a preferred embodiment, called the "stacked independent bead traction cable conduit" is illustrated in FIG. 5 and consists of compression-resistant torroidal beads or rings [10] which are threaded on a tether [1], such as a cable, to form a compression sheath. These are preferably of a hard, biocompatible material. These are not necessarily attached to each other but are held in place by the tether traversing the hole penetrating each bead. FIG. 5a is a longitudinal interrupted section of a tether and sheath; FIG. 5b is an enlarged longitudinal section of a short segment; FIG. 5c is a perspective view of a short segment at one end, with the tether protruding from the end of the stack of beads. 5d is an individual bead.

Rings or beads may be of any aspect ratio. That is: they may be longer than wide and appear as tubular segments; they may be spheres with a hole through the center; they may be flat, ring or doughnut (torroid) shaped, an so on.

Figure 6A:
FIG. 6 illustrates various configurations of the individual beads of FIG. 5.
Figure 6B:
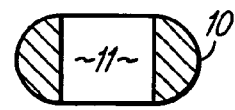
Figure 6C:
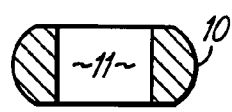
Figure 6D:

The cross section of one side of beads may be of various profiles, with non-limiting examples being (a) round (FIG. 6a), (b) segments of circles (FIG. 6b), (c) 'D' shaped (similar to a segment of a circle, but flattened at each end to increase the bearing surface, FIG. 6c), or (d) rectangular (FIG. 6d). Each has a channel [11] for the tether.

The configuration of 'c' (i.e., 'D'-shaped) is preferred because it:
1. has a larger bearing surface to sustain compressive stress than does examples 'a' and 'b'
2. has a bending point much closer to the tether's axis of tension than does example 'a', thus creating less of a length-varying effect on the overall conduit, relative to the tether, during bending
3. offers stable structural support from a broader mid-section than would example 'd' for the same contact surface.
4. conversely to point 3 above, compared with an example 'd' profile with the same mid-section, profile 'c' creates much less of a lengthening effect on the overall sheath during bending Further, there are several other variations—i.e., potentially improving modifications or additions—to the 'stack of beads' concept for a traction conduit:
A. See FIG. 7. The stack of beads [1] may be enclosed in a openly woven or braided tubular jacket [12], or a multiply perforated elastomeric jacket, or other tube not restrictive of fluid flow-through. This would serve to hold the segment together to facilitate assembly and yet allow ingress and egress of tissue fluid. This organizing jacket sheath for the bead traction cable conduit may be made either of a bioabsorbable material or a biocompatible nonabsorbable material.

Figure 8A:
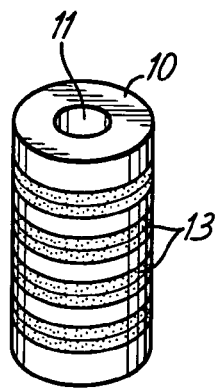
FIG. 8 shows an absorbable adhesive, which holds beads of FIG. 5 aligned to facilitate fabrication and implantation.
Figure 8B:
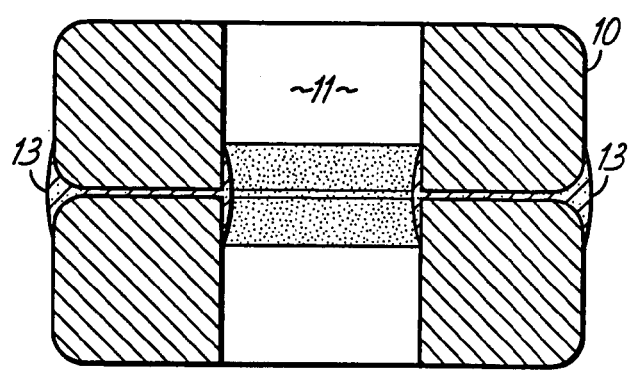

B. See FIG. 8. The stack of beads [10] may be adhered to each other by a readily soluble or removable adhesive [13] or shell for the same purpose as the jacket described above; 8a is a perspective view of several beads, and 8b a section of two beads, with such an adhesive.

Figure 9A:
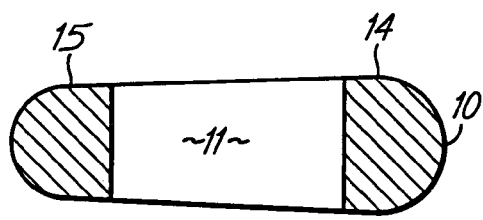
FIG. 9 is an independent bead conduit in which beads are asymmetric to allow self-alignment according to curvature required anatomically.
Figure 9B:
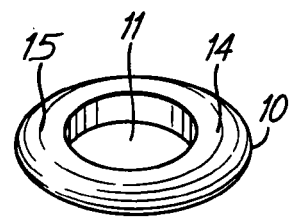
Figure 9C:
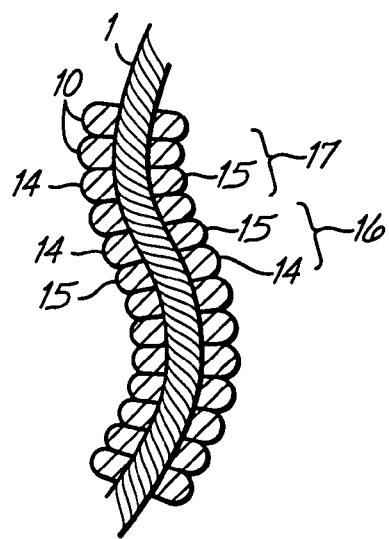
Figure 14A:
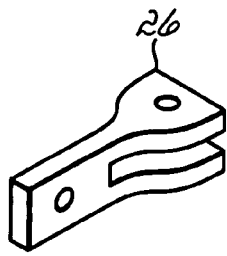
FIG. 14 is a series of hinged links to allow flexible conduction of rotary power in the body.

C. See FIG. 9. The stacked independent bead traction cable conduit may include at least one or more of the torroidal beads that is eccentric—thicker on one side than the other, where 'thickness' is defined as the aspect in the direction parallel to the tether—to allow for random reordering and rotating to conform to a curvilinear path during use. Since (a) the beads may freely rotate on the tether once in place (in the event the tubular jacket described above is employed, rotation would require the jacket, or a bonding between bead and jacket, to be soluble or absorbable), (b) there is a repetitive expected compressive force between adjacent beads in a sheath, and (c) the cyclic compression and release will have somewhat of a 'shuffling' effect on the structure, allowing rearrangement of geometric relationships to the most mechanically stable (lowest energy) configuration—then beads will tend to migrate so that shortest sides are aligned with the lesser curvature of any sustained bend in the overall sheath structure until spacing between beads along the greater curvature has been eliminated. Depending on the ratio of rotated beads in any given direction, the gross configuration of the conduit in any region could assume a curvature ranging from straight (equal numbers of beads having their thick-thin axis oriented in any pair of opposite directions) to a radius of centerline curvature equal to half the diameter of one bead face along the thick-thin axis plus the product of half the minimum face-to-face bead thickness and the ratio of the face-to-face thickness differential to the midpoint bead thickness. FIG. 14a is a cross section of such a bead with the aspect [14] of the bead on the right side of the sketch being longer from top to bottom as drawn than is the aspect [15] of the bead on the left side of the sketch. FIG. 9b is a perspective view of such an asymmetric bead, and FIG. 9c a longitudinal section of a segment of beads. In that section it will be noted that there are no substantial paces between beads on either side of the tether channel, and the majority of beads are rotated so that their shorter aspects are on the side of the concave curvature [17]. In relatively straight sections [16], the bead orientation will tend to alternate, so that over a several-bead segment, cumulative lengths on all sides will be approximately equal. These orientations may be achieved simply by placing the beads on the tether in random orientation and allowing them to equilibrate to the most stable, lowest energy configuration. In a biologic implantation, the entire bead compression sheath and tether assembly would be positioned, and position adjusted to anatomic requirements, followed by a period of cyclic actuation to induce self-adjustment, and followed in turn by length adjustment of the tether to accommodate the re-orientation and change in tether length.

Figure 10:
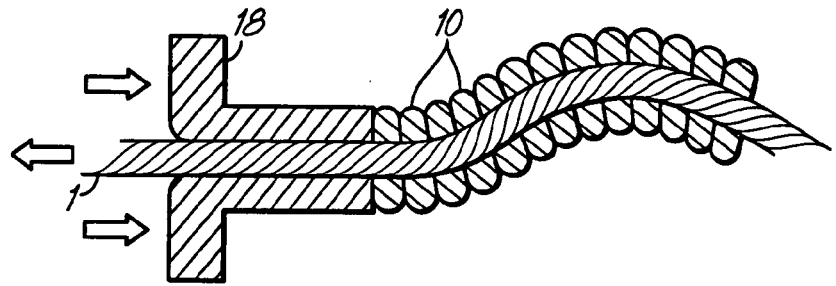
FIG. 10 is an adaptor to facilitate connection of traction conduits such as the independent bead type.

D. If bead configuration does not allow satisfactory fixation at one or both ends of the tether/compression-sheath assembly (i.e., at the power-driver and/or the driven-device end), then a length of rigid tubing [18], coil-type sheath, or other appropriate device with suitable channel to accommodate the tether, is placed over the end of the tether [1] beyond the beads [10]. This device is used for fixation to the power-driver and/or the driven-device. See FIG. 10, a non-limiting example of such a device.

Figure 11A:
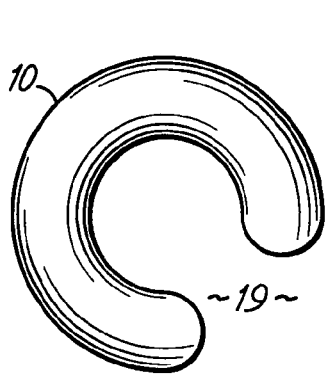
FIG. 11*a-c* are independent beads for a conduit such as that of FIG. 5 that allow free ingress and egress of tissue fluid.
Figure 11B:
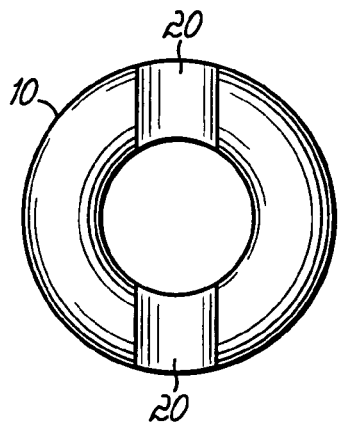
Figure 11C:
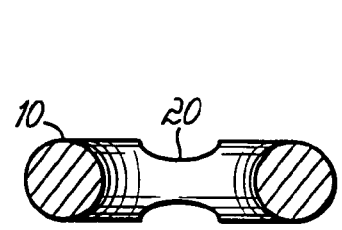

E. See FIG. 11. Based on the same rationale that was given for the embodiment of FIG. 7—to allow ingress and egress of tissue fluid—beads [1] may either be interrupted at one point [2] in their circumference (that is, extend about a subtotal arc of a circle rather than a complete circle, 16a) or have radial grooves [3] (16b, a top view and 16c, a section).

F. Materials may vary. A stacked independent bead traction cable may be comprised of beads made of (1) a ceramic such as pyrolytic carbon, (2) a hard polymer such as polyacetal (3) a hardened composite such as glass or metal-filled epoxy or (4) any other material of appropriate bioreactive and mechanical properties.

Figure 12A:
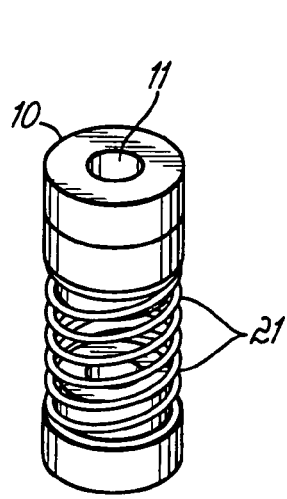
FIG. 12 is a stacked independent bead traction cable conduit modified to incorporate an energy-storing spring support
Figure 12B:
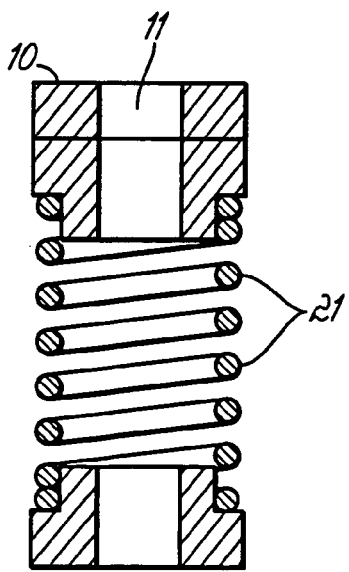

G. See FIG. 12. The stacked independent bead [10] traction cable conduit may be modified to incorporate an energy-storing spring support [21] holding at least some adjacent beads separated for the purpose of absorbing and storing mechanical compression energy during rapid loading, with release of energy to actuating units at a rate determined by mechanical impedance. FIG. 12 is a non-limiting example in which the spring is helical.

Conduits of Rotational Motion

Figure 13A:
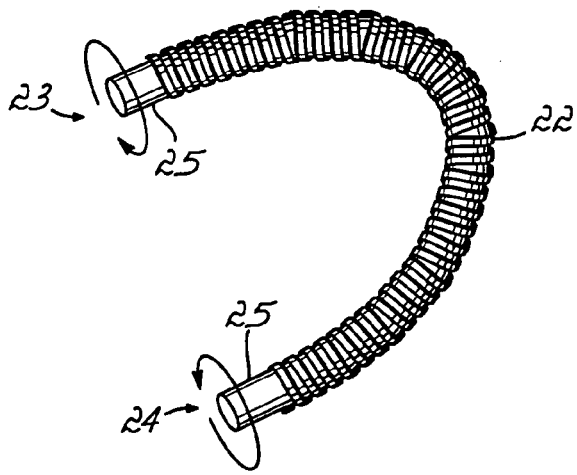
FIG. 13 is a conventional helical flexible shaft for transmitting rotary power, which has been adapted for use in the body by separating turns to allow ingress and egress of fluid and addition of a central tightening-resisting member such as a cable.
Figure 13B:
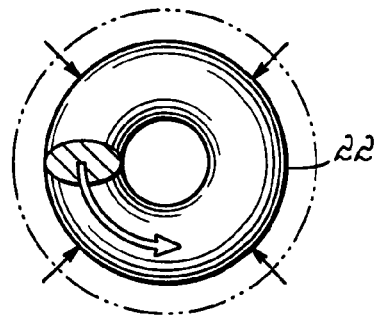
Figure 13C:
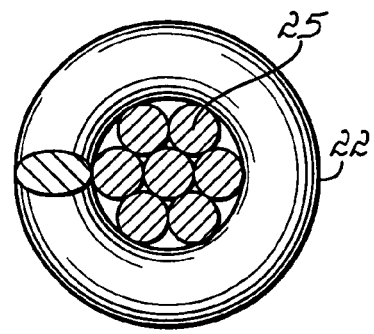

See FIG. 13. A flexible shaft power conduit system for rotation of selected links of the train-of-links actuator described above may be comprised at least in part of a helix of a material such as a metal wire, glass fiber, or polymer. The helix [22] is configured so that rotation of the driving end [23] produces rotation at the driven end [24]. Coupling structures such as rods [25] facilitate transmission of torque and rotational movement into and out of the conduit.

If the direction of torque, as viewed from the driven end [23] is the preferred direction, opposite to the sense of the helix (i.e., a clockwise torque delivered to a helix that proceeds counterclockwise as it proceeds away from that end), then the load is borne largely by tension in the helix [22] turns approximately equal to the transmitted torque divided by the mean radius (average of inside and outside radii). A potential failure mode, tightening the helix to a smaller radius, may be countered by placing a flexible structure [25] such as a cable in the center of the helix. Alternatively, this core flexible structure [25] may be one or more monafilament flexible members such as polymer or wire strands aligned generally parallel to each other rather than being twisted or braided into a cable.

As yet another alternative, the helix turns may be in two, three, or more layers with adjacent layers being in opposite directions. That is, an inner helix, with or without a still more inner core, may be clockwise, a second helix may be counterclockwise, a third one clockwise, and so on.

In the arrangements above, materials may be alternated to improve wear. For example an inner and second helix may be titanium and glass fiber, respectively. For another example the first and second members of a double helix may be a cobalt-chromium alloy and linearly crystalline polyethylene (e.g., Spectra®, Dynema®, etc.), respectively.

Delivery of a torque in the direction opposite that described will tend to produce an 'unwinding' of the helix as the torque's magnitude increases, effectively limiting the torque capacity to less than that in the preferred direction.

A multiple (double, triple, and so forth) helix may be employed as a variant to allow sharing of this tensile load and thus alter mechanical properties of the helix for a given outside radius and a given wire (or other material) thickness.

A series of the solid torroidal or cylindrical bearing similar to those described above and illustrated in FIG. 4 for traction conduit application may also be used for a core [25] for torsion conduits as a measure to improve wear characteristics. As an alternative in this application, these may be solid cylinders.

Similarly the stacked beads described above and illustrated in FIG. 5 for traction conduit application may be modified, generally in a larger caliber, and used as a containing mechanism for torsion conduits to counter tendency to unwind if the torsion conduit is applied in the direction not optimal for its sole layer or outer layer. In such a use, the beads may be modified by addition of an outer layer of a material chosen for tensile strength—such as an outer band (possibly similar to a barrel hoop) of metal or of wound high-strength polymer fiber. The body of the bead may or may not be constructed of a material chosen for compression resistance, such as a ceramic.

Figure 14B:
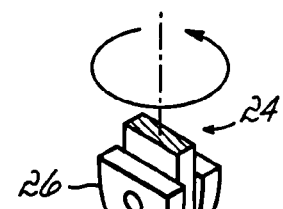
Figure 14B:
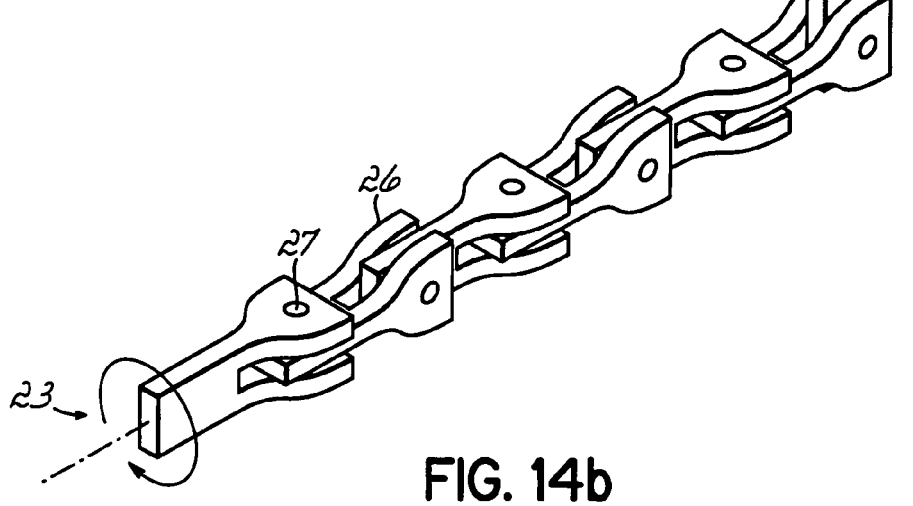

See FIG. 14. Alternatively, the flexible shaft conduit may be comprised at least in part of a series of links [26] joined so that they may freely turn in one plane relative to each other by means of pins [27] or other mechanism well known to and commonly applied by those in mechanical design. This functions similarly to the helical conduit just described to deliver rotational movement from a driving end [23] to a driven end [24]. However, there is not a preferred direction, as tolerated loads should be generally similar in both clockwise and counterclockwise directions.

It will be understood that a rotational or torsion power conduit may be used to deliver power to a traction-mediated heart actuator. This may be chosen if rotary drivers such at that in FIG. 19 below prove more practical in extended experimental and/or clinical trials than direct traction drivers, while advantages are shown for traction activated heart drivers for at least one ventricle. This may also be chosen if wear characteristics of rotary conduits prove in experimental assessment to be superior to traction conduits, whether for reasons of lower normal stresses on sliding surfaces or for other reason.

See FIG. 15. A system of embedded solenoids may be configured for inducing rotation of at least one region of a train-of-links actuator [28], which is positioned to cyclically deform an active-jacket [29] component of a heart-wall repowering system for circulatory support. That is, electrical to mechanical energy conversion and conduction of that energy to the actuator may be concentrated at the site of the actuator (as opposed to the usual arrangement of energy conversion outside the chest and mechanical transmission). In a train-of-links actuator [28], it is possible to produce prescribed deformation of the entire train by rotation of one or more 'junctional' links [30]. This may be accomplished by equipping the junctional link [30] with hubs [31] on at least one side, with embedded permanent magnets having north [32] and south [33] poles. A solenoid-equipped socket [34] surrounds each hub [31] (shown in functional position in FIG. 15a and on the left part of FIG. 15b, and separated or 'exploded view' on the right part of FIG. 15b). The socket has regions that become magnetized to south [33] and north [32] poles upon electrical power delivery through conductors [35]. This effects rotation of the junctional block [30] and thus induces the deformation of the actuator [28] and the jacket [29]. The hub [31] and the junctional block [30] may either be rigidly joined or have an intermediate deformable spring coupling [36], which may be a spiral (clock-spring type), torsion bar, helical, or other type which transiently stores mechanical energy to allow actuator [28] deformation to be influenced by impedance of the jacket [29] and heart wall.

In an alternative not illustrated, the hub [32] may contain multiple permanent magnets and the socket [34] multiple solenoids of alternating polarity. This arrangement becomes the equivalent of a low-speed direct current electrical motor in which the solenoids of socket [34] are the field coils and the permanent magnets of hub [32] are the armature. Rate of actuation may then be controlled by timing of solenoid activation.

A combination of some of the above principles and techniques is embodied in yet another alternative. In this an implanted guarded reel of the type shown in FIG. 22 and the accompanying text, or any other converter of rotary to linear motion commonly used in nonmedical applications such as a screw mechanism, may be adapted for implantation according to the principles stated above. This allows the advantages of rotary energy production and transfer to be achieved while driving an actuator on the heart that is directly driven by linear displacement.

Power supply mechanisms may be electromechanical converters or delivery mechanisms of skeletal muscle power.

Electromechanical Conversion Mechanisms.

An electromechanical converting unit may be intended and suited for implantation in the body, preferably outside the chest cavity, receiving electrical power from either an inductive transcutaneous electrical inductive transfer system or a percutaneous conducting cable or an intracorporeal source such as a battery, and delivery of mechanical power through one or more power conduits of any type described above. More than one similar or dissimilar subunit may be combined in either an integrated or modular fashion. The converting unit may be constructed in such a way that it is powered by electrical energy in the range of 6 to 20 Watts and which delivers 0.8 to 4 Watts of mechanical energy expressed as the product either of rotational angle and torque or of translational distance and force for a conversion efficiency in the range of 10 to 30%.

There are variations in many characteristics of power supply mechanisms. These variations may occur in several combinations, either from one device to another or in different components of the same device. That is, for example, in a biventricular assist system, a driver may deliver rotational motion generated through a motor and gear assembly and transmitted through its housing via magnetic coupling and then through an appropriate conduit to an actuator for left ventricular assistance—while also delivering translational motion via a physical coupling through a conduit to a right ventricular actuator.

There are variations in:

1. Type of motion produced.
   a. Translational. Several versions of electromechanical conversion mechanism may be suited for driving either the articulating link or the direct traction class of actuators. Mechanisms (motors, solenoids, springs, etc) are discussed below. Translational motion producers will cause a relative motion of tether and conduit in the general range of 5 mm to 40 mm (approximately 0.2 to 1.6 inches), against a maximum resisting force in the general range of 45 to 180 Newtons (approximately 10 to 40 lb). This will be repeated at intervals of generally 400 to 1200 msec (i.e., at rates of 50 to 150 per minute) with activation completed generally within 10 to 40% of the complete cycle. Frequency and velocity of activation may be fixed or may be controllable my systems and algorithms to be described later.
   b. Rotational. The converting unit may be constructed in such a way that mechanical output is cyclic rotation of a flexible coupling. Rotational motion producers will cause a relative rotary motion of tether and conduit in the general range of 1 to 2 radians (approximately 58 to 116 degrees)), against a maximum resisting moment in the general range of 4 to 8 Newton-meters (approximately 36 to 72 lb-inches). Frequency, active cycle fraction, and control comments given immediately above for translational motion apply equally to rotational motion.

2. Interface with tissue: i.e., whether conversion mechanism is:
   a. enclosed in a housing with force transmitted out via a physical coupling (examples: sliding shaft through port—e.g., FIG. 16—, coupling mounted on flexible diaphragm—e.g., FIG. 17—) (figure: 16a shaft in, 16b shaft out)

Example of FIG. 16: Energy may be transferred from a electromechanical converter by physical couplings, which slide back and forth, or rotate back and forth within a port of socket in the housing wall. That is, the converting unit may be constructed in such a way that a tension or a compression spring contained in the housing stores mechanical energy for release at a rate determined by mechanical impedance. (In a nonlimiting illustration of the sliding coupling concept, FIG. 16a shows a shaft [37] retracted into, and 16b a shaft protruded further out of, a housing). The converting unit may be constructed in such a way that at least one compression sheath [2] is fixed relative to the power unit by a rigid strut [38], allowing tether (e.g., a cable) [1] to be cyclically moved within the compression sheath [2]. The housing is filled with a gas or lubricating fluid [43]. Regions [39] of the housing may be flexible, allowing expansion and retraction to compensate for the volume change with shaft movement. FIGS. 26c and d are sectional views also showing a motor [40] and a cam or gear mechanism [41], which impose movement onto the shaft.

Figure 17:
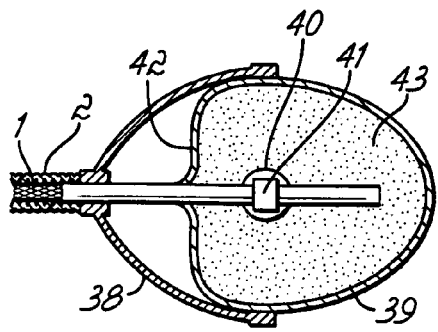
FIG. 17 is another mechanism by which energy may be transferred from a fluid-filled electromechanical converter across a flexing region of the housing wall, such as a bellows or inverting sock.
Figure 18A:
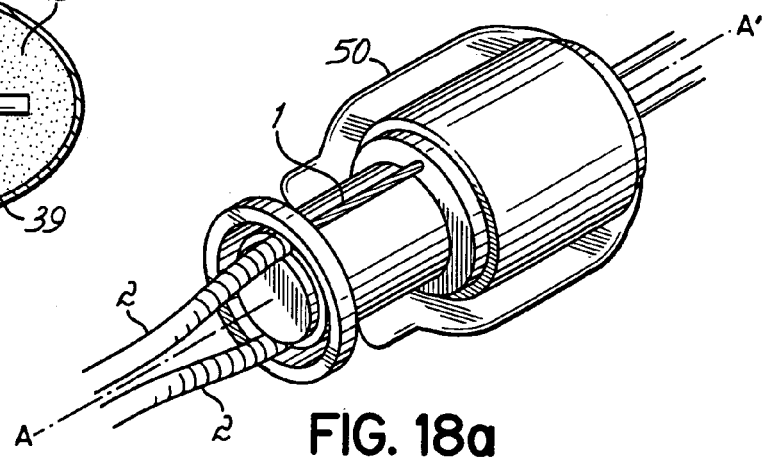
FIG. 18 is a low-speed linear electric motor configured for use directly in tissue in which field coils are hermetically sealed and on which a permanent-magnet containing slider, propelled by changing activation of the field coils, delivers linear displacement power to a conduit.
Figure 18B:
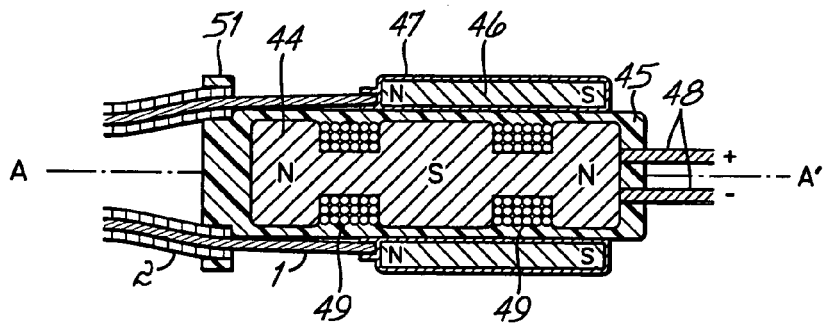
Figure 18C:
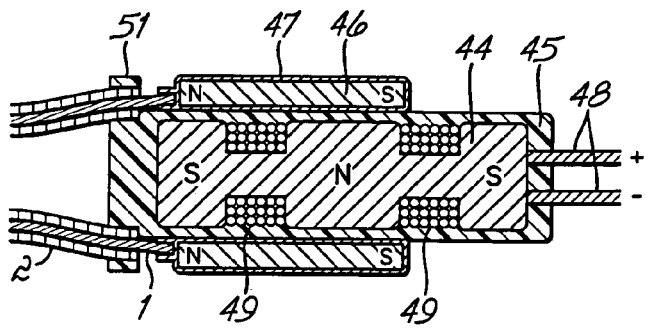
Figure 18D:
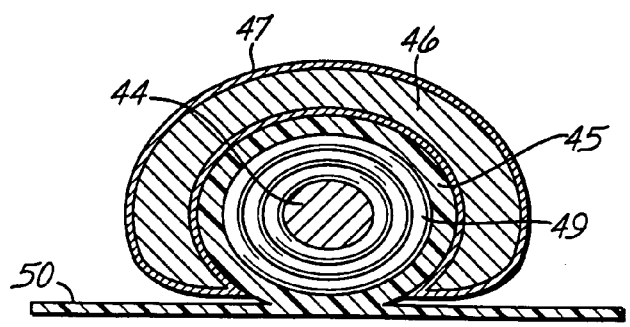
Figure 19A:
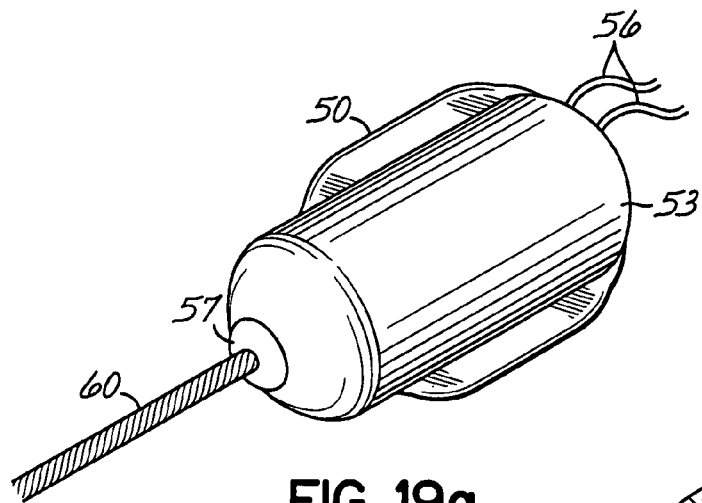
FIG. 19 is a low-speed rotary electric motor configured for use directly in tissue in which a permanent magnet-containing armature rotates in a socket or tunnel within a hermetically sealed housing, such as a ceramic, containing field coils.
Figure 19B:
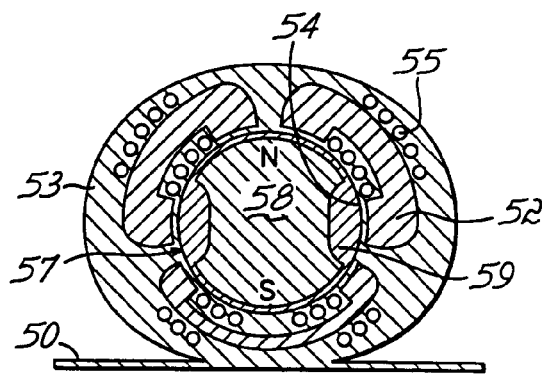
Figure 19C:
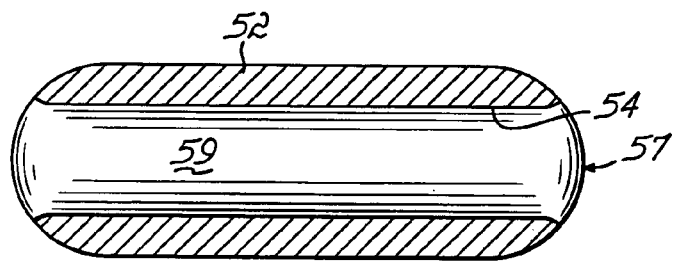
Figure 19D:
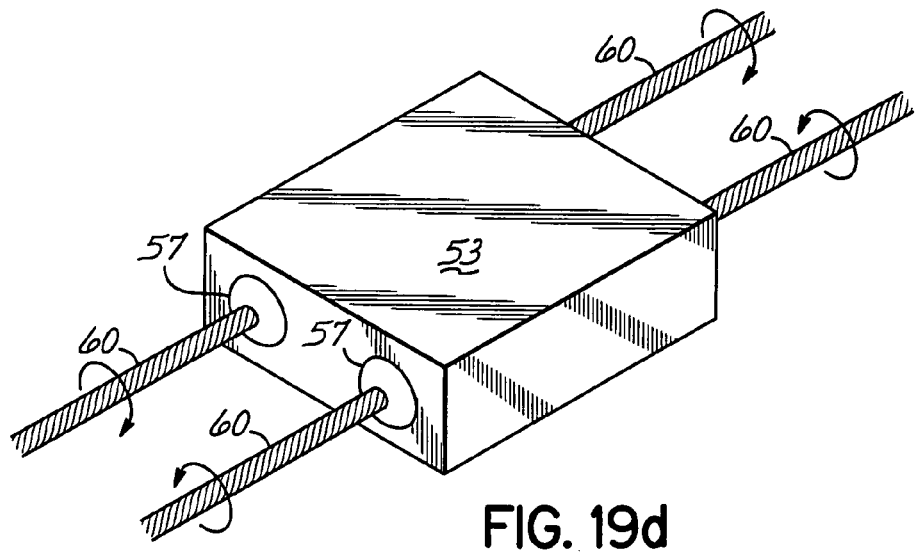

Example of FIG. 17: Alternatively, energy may be transferred from a electromechanical converter by physical couplings which are fixed to the housing but which may move as that section of the housing moves relative to the remainder of the housing body, such as by elastic deformation. That is, the converting unit may be constructed in such a way that the means of energy transmission from inside the housing to outside it is a cyclically flexing region [42] of the housing wall—such as a simple nonrigid location, a defined diaphragm, or a bellows—the inside of which is mechanically linked to the power unit (such as the motor [40] and cam or gear mechanism [41] shown) and the outside of which is mechanically linked to at least one energy transmission traction cable [1] inside a compression sheath [2] which is joined to the housing body by a rigid strut [38], allowing the housing to be hermetically sealed. The housing is filled with a gas or lubricating fluid [43], and at least one somewhat flexible and compliant region [39] of the housing wall must be provided to allow compensation for the volume changes with physical coupling movement. A nonlimiting example is a translational coupling, which is mounted on flexible diaphragm. (FIG. 17a diaphragm in, 17b diaphragm out).
   b. enclosed in a housing with force transmitted out via magnetic coupling (examples: rotating sliding member on housing, rotating member on housing with tether/shaft fit to member)

In yet another alternative, a power source may be enclosed in a housing with work (force and linear displacement or torque and angular displacement) transmitted out via magnetic coupling. This requires a changing magnetic field at the surface of the housing, generated within the housing.

One way to generate a changing magnetic field is by alteration in the pattern of solenoid activation with time. This requires a moving member outside the housing, which is connected to the conduit. For linear displacement transmission, a 'slider' outside the housing, such as the nonlimiting example of FIG. 18 which may move back and forth but not escape due to mechanical constraints is employed.

FIG. 18 shows such a mechanism transferring linear displacement motion: 18a is a perspective view, 18b a sectional view along the A-A' axis of 18a in extension (tether relaxed) and 18c the same sectional view in retraction (tether pulled in). 18d is a sectional view along the B-B' axis of 18a.

Solenoid [44] is encased in housing [45] which may be a ceramic, a polymer, or other material. Permanent magnet [46] is encased in its own housing [47] of either similar or dissimilar material, chosen for limited sliding and static friction with regard to the solenoid housing [45]. Permanent magnet [46] and its housing are configured to slide on the surface of solenoid housing [45] from the extension to the retraction position upon reversal of electric and magnetic polarity of the solenoid (by means of electric lead wires [48] and windings [49] and to return to extension position upon restoration of original polarity. The movement of permanent magnet from extension to retraction pulls tether [1] which may be a cable, chain, or other flexible tension member contained in a sheath or housing [2] such as described above for a power conduit. There may be one, two (as in the example) or more tethers and sheaths for each permanent magnet, one or more permanent magnets for each solenoid, and one or more solenoids for each power unit. The solenoid housing may have a flange or tabs [50] to facilitate fixation to anatomic structures such as abdominal wall fascia. Tether sheaths [2] may be secured to solenoid housing [45] by one or more fixation bands [51].

Note that the single solenoid and double-ended solenoid of this example may be replaced with multiple solenoids and magnets to be a linear electric motor in which the field windings are comprised of solenoids [44] hermetically sealed in the housing [45] while the armature is comprised of the permanent magnets [46] in their sealed housing [47] sliding on the solenoid housing [45].

FIG. 19 is an example showing this mechanism transferring rotary motion: Another nonlimiting example of magnetic coupling across the housing of a hermetically sealed solenoid is the 'rotator' of FIG. 19, which also may move back and forth but not escape due to mechanical constraints. 19a is a perspective view, 19b a cross section, and 19c a long section.

One or more solenoids [52] (or field coils) are encased in a housing [53] with their poles near the surface of a generally cylindrical channel [54], which passes all, or part of the way through the housing. Windings [55] of the solenoids are supplied by lead wires [56].

Within the channel is a generally cylindrical armature [57] consisting of one or more permanent magnets [58] in a housing [59]. Upon activation of the solenoids [52] the armature [57] will be caused to rotate by the magnetic field, thus turning the flexible shaft [60] or shafts, which are attached to one or both ends of the armature. This may be in a single, near instantaneous rotation in the case of a single solenoid and single armature magnet (generally requiring energy storage and release by other mechanisms described herein) or stepwise motion in the case of multiple solenoids and magnets, with some degree of motion smoothing due to rotational inertia in either case. Multiple units may be combined as in the nonlimiting example of 24d in which two armature channels [54] armatures [57] and two sets of solenoids [52] may be present in a single solenoid housing [53].

It will be apparent that synchronous or asynchronous activation of solenoids will result in all armatures turning. In the example of 24c, each of the two armatures has two flexible shafts, with one shaft of each armature caused to rotate clockwise and the other counterclockwise when activated, followed by either passive or active reversal in the opposite direction.

Another way to generate the changing magnetic field is by physically moving a magnet inside the power supply housing.

Figure 20:
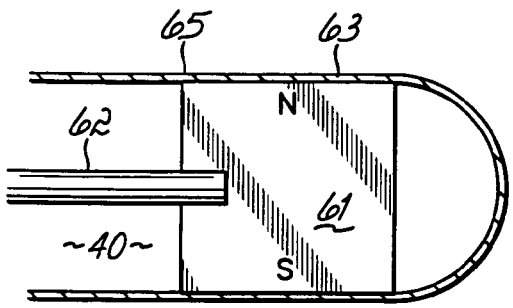
FIG. 20 is an interface by which linear motion of a member inside a fluid-filled housing is transmitted to a sliding member outside the housing by magnetic linkage.

One nonlimiting example is a moving magnet coupled across housing wall to a linear traction conduit. FIG. 20 is a long-sectional view of one non-limiting example.

A permanent magnet [61] is mounted on a shaft [62], which is propelled back and forth (by a motor or other power source, not shown) within a housing [63] filled with a gas or lubricating liquid [64] such that the magnetic field at the housing surface [65] changes. An external permanent magnet in a sliding housing, not shown here but as illustrated above for the solenoid-activated device of FIG. 18 is thus caused to slide back and forth, driving a traction power conduit.

Figure 21A:
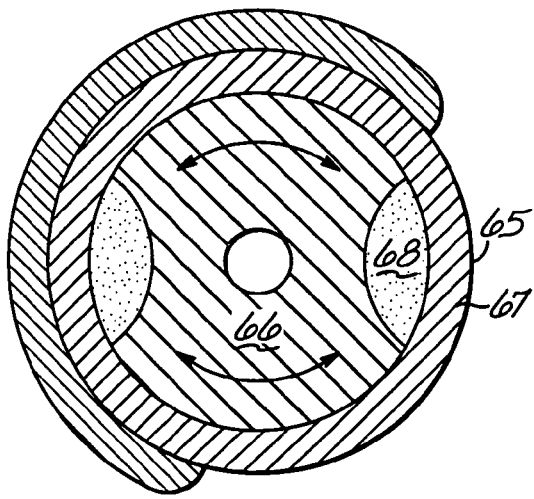
FIG. 21 is an inter interface by which rotary motion of a member inside a fluid-filled housing is transmitted to a rotating member outside the housing by magnetic linkage.

Yet another nonlimiting example is a moving magnet coupled across housing wall to a flexible rotary shaft conduit. FIG. 21a is a cross-sectional view of one non-limiting example.

A shaft-mounted permanent magnet [66] is rotated back and forth (by a motor or other power source, not shown) within a housing [67] filled with a gas or lubricating liquid [68] such that the magnetic field at the housing surface [65] changes. An second, driven, external permanent magnet in a rotating housing, as illustrated above for the solenoid-activated device of FIG. 19 is thus caused to rotate back and forth, driving a flexible shaft or other rotating power conduit.

Figure 21B:
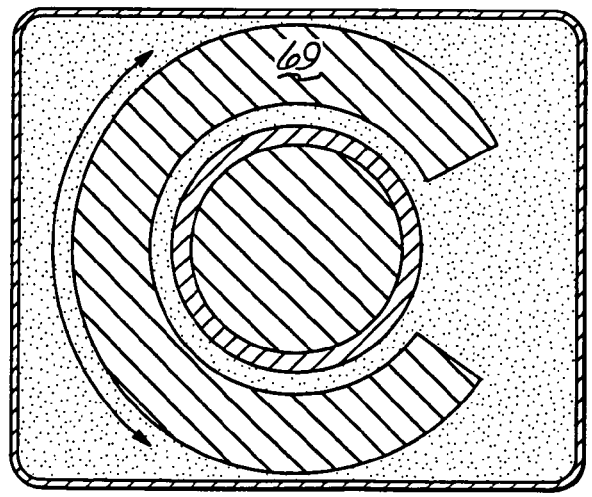
Figure 22A:
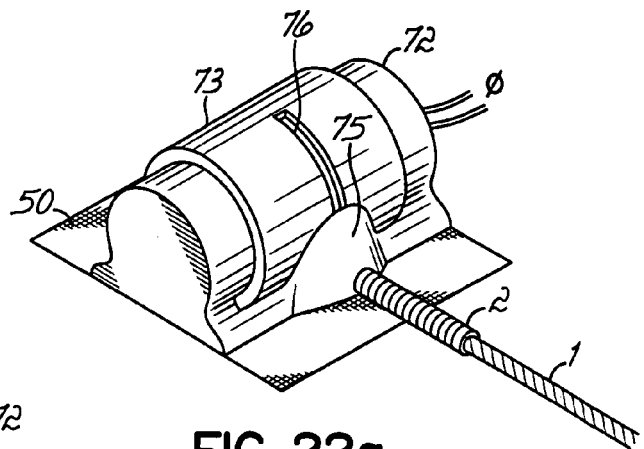
FIG. 22 is a low-speed rotary electric motor in which field coils are confined to a hermetically sealed housing and a surrounding permanent-magnet containing armature rotates a partial turn with activation, winding a length of a tether to transmit linear energy.
Figure 22B:
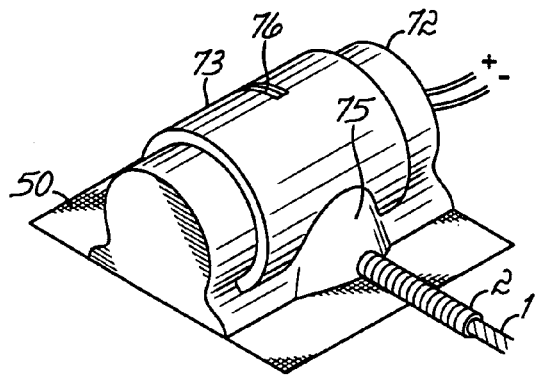
Figure 22C:
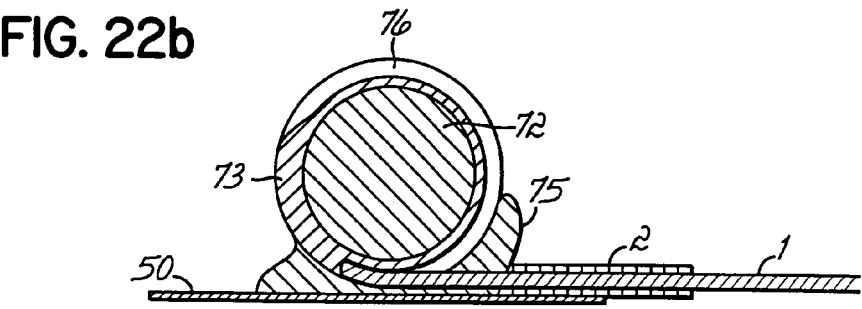
Figure 22D:
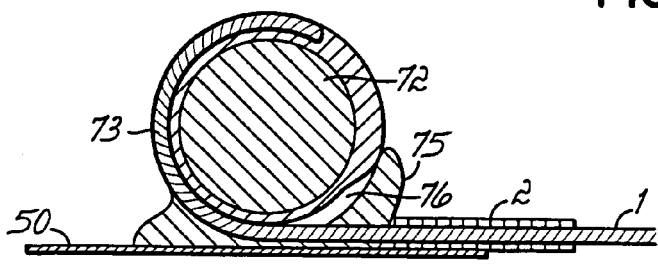
Figure 22E:
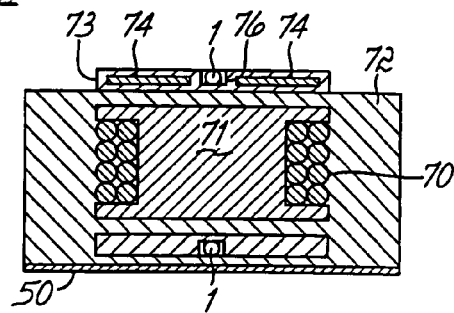
Figure 23A:
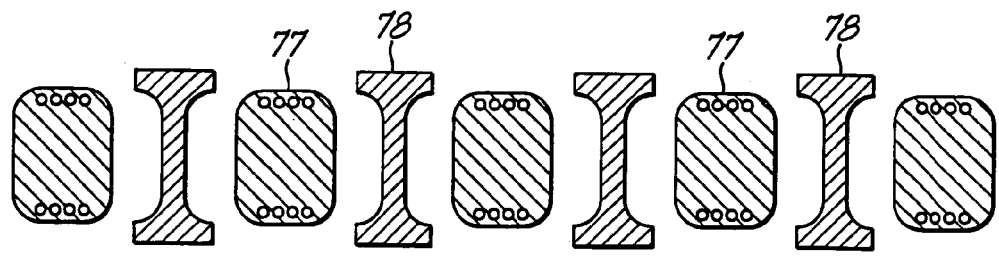
FIG. 23 is a sectional view of a linear stack of several solenoids which shorten upon activation, are each hermetically sealed, and which may be activated in any pattern to control rate of overall shortening, and configured to promote a favorable biologic response similar to the pseudosynovial capsules that surround artificial joints.
Figure 23B:
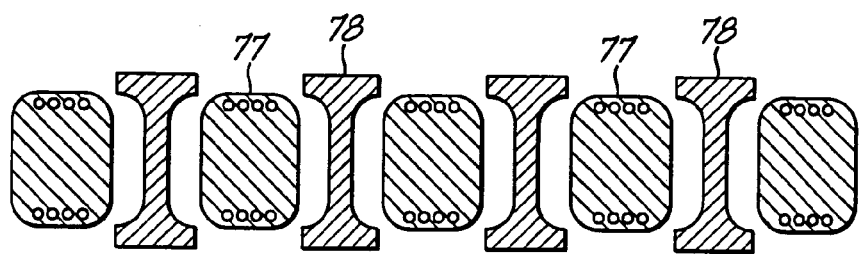
Figure 23C:
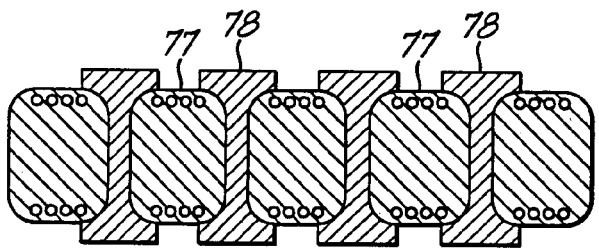

Alternatively, as shown in the cross-sectional view of another non-limiting example of FIG. 21b, the passively driven permanent magnet armature may be within a cylinder that is surrounded by a reciprocally rotating magnet (driven by any available source, such as a motor or a harnessed skeletal muscle) in a concentric external shell [69] outside the housing of the cylinder.

c. set directly in tissue (examples: winding spool with guard—e.g., FIG. 22, stacked solenoid—e.g., FIG. 23.)

A further alternative embodiment of magnetic transmission from a hermetically sealed source to an energy transmission conduit is a low-speed rotary motor in which field coils [70], with or without low-permeability core [71] are embedded in a cylindrical housing [72] surrounded by a concentric shell [73] containing one or more permanent magnets [74] and functioning as an armature. Upon activation, the rotating armature shell winds a cable [1] or other type of traction tether several mm (generally half to one rotation, possibly more), generally through a conduit sheath [2]—from the position shown in 22a and 22c, perspective and cross-sections, respectively, to the position shown in 22b, 22d, and 22e, respectively, perspective, cross- and long-sections, respectively, and then releasing. The armature shell may be a complete cylindrical section as illustrated in FIG. 22 or a subtotal arc. 22a is a perspective view and 22b a cross sectional view. Tabs of fabric or other material [50] provide points for fixation to tissue. A bracket [75] anchors the sheath [2] of a traction power conduit and fixes its position relative to the field coil housing [72]. The armature shell generally has a grooved channel [76] in which the tether may lie as it is wound.

The rounded shaping of components and their interfaces, including that of the cable with the block component, are designed to promote a favorable biologic response similar to the pseudosynovial capsules that surround artificial joints.

Figure 24:
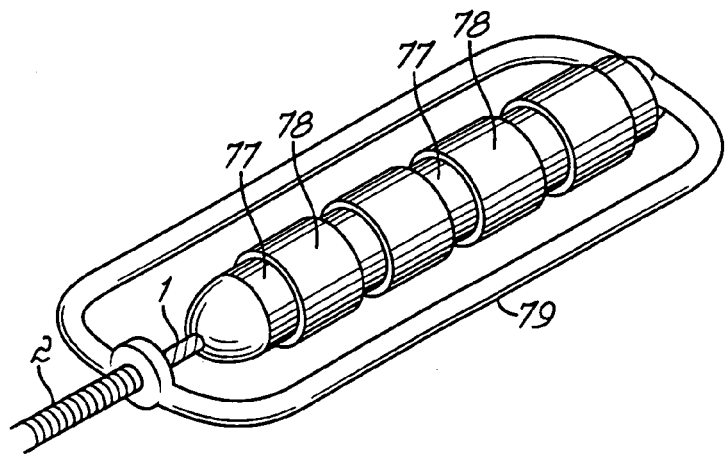
FIG. 24 is a perspective view of a stack of solenoids configured with a bracket to facilitate use in activating a tether-in-sheath linear energy onduit.

Another alternative is shown in FIGS. 23 and 24. This allows electrical components to be hermetically sealed while physically delivering linear displacement power distributes individually sealed components in tissue, and is arranged to allow those components to move in a fashion designed to promote a favorable biologic response similar to the pseudosynovial capsules that surround artificial joints. This is an assembly of stacked solenoids [77] alternating with permanent magnets [78]. Both solenoids and magnets are encased in hardened, high impact, biocompatible, wear-resistant polished material, preferably ceramic, e.g. either pyrolytic carbon (track record in heart valve prostheses with similar loading in similar environment) or some ceramic with satisfactory track record in prosthetic femoral balls. One set (solenoids as illustrated, alternatively permanent magnets) are simple discs with N one side, S other. Other (vice versa, pm's or s's) are discs with short cylindrical flanges with widths—to either side—half the opposite type of disc's thickness. There are multiple fenestrations in flanges for egress and ingress of tissue fluid. Activation produces very rapid, forceful shortening of the stack of an amplitude equal to the product of individual disc-to-disc displacement and number of total discs.

The long section of 23 shows a simple stacked configuration at progressive stages of shortening as progressively more of the solenoids are activated.

The perspective view of 24 shows a perspective view of one possible configuration in extension (relaxed). Lead supply wires are a necessary component but not shown in the drawing. A traction tether [1] is connected to one end of the stack of solenoids/magnets. A bracket [79] connected to the other end extends to stabilize and fix the relative position of a compression sheath [2] through which the traction tether passes.

3. Mechanism of electromechanical conversion:
   a. motor with gear assembly or cam. Any direct current or alternating current high or low speed motor, with a gear, cam, or other mechanism adapted from those very familiar to those knowledgeable in the field of electromechanical design for other applications may be used to convert electrical to mechanical energy suitable for turning a flexible shaft, pulling or pushing a traction power conduit, and/or driving a hydraulic mechanism for altering heart wall dimensions consistent with this invention. The motor may be enclosed in a housing and bathed in a lubricant liquid or a gas.

Adaptations required are those of (a) compact size (generally less than 500 ml displacement) and (b) long durability (generally at least one year of continuous function at 60 to 120 cycles per minute, or about 60 million to 120 million cycles), supplying quantities of power outlined above. The physical placement of such adapted motor and gear/cam assemblies would be in a housing filled with gas or preferably lubricant fluid as illustrated in FIGS. 21 and 22, equipped for out-transfer of generated power mechanically.

Alternatively, FIG. 20, described above. shows a nonlimiting example of how such a motor with gear or cam assembly (not drawn) might drive a moving magnet coupled across housing wall to a linear traction conduit. FIG. 21 above shows a nonlimiting example of how such a motor with gear or cam assembly (not drawn) might drive a moving magnet coupled across housing wall to a flexible rotary shaft conduit.

b. Solenoids. The principle mechanical issue confronting solenoid application is control of force delivery rate, considering the near instantaneous activation of a solenoid and mismatch of this with demands of impedance of an actuated heart wall. Embodiments of this invention teach two means of accomplishing this:
i. energy storing spring mechanism (translational and rotational examples) (FIG. 25 shows a translational or tension spring in 3 stages, FIG. 26 and FIG. 27 show torsional and compression springs similarly in 3 stages)

Figure 25A:
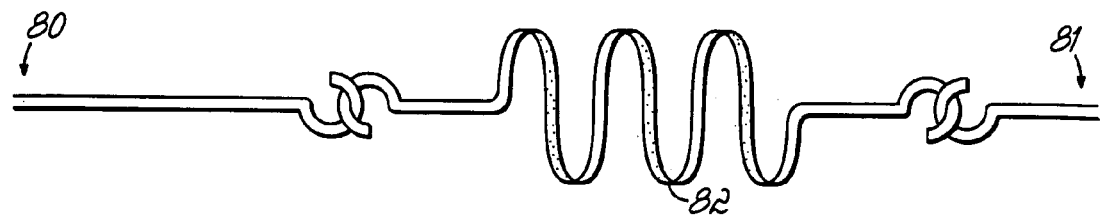
FIG. 25 is a tension spring for storing translational energy in 3 sequential stages of its cycle. This may be located at any point between generation of energy (such as a motor, a solenoid, a skeletal muscle harnessing de vice, or other) and delivery to a heart-wall actuator.
Figure 25B:
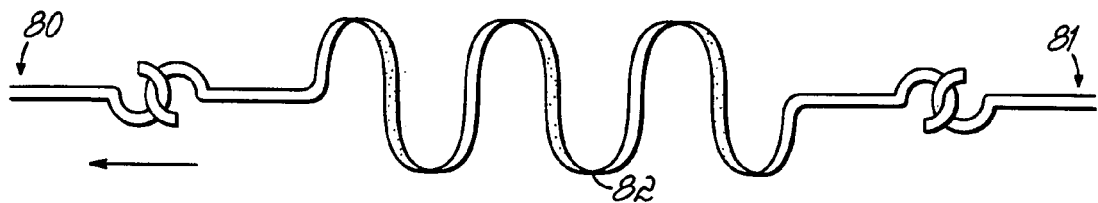
Figure 25C:
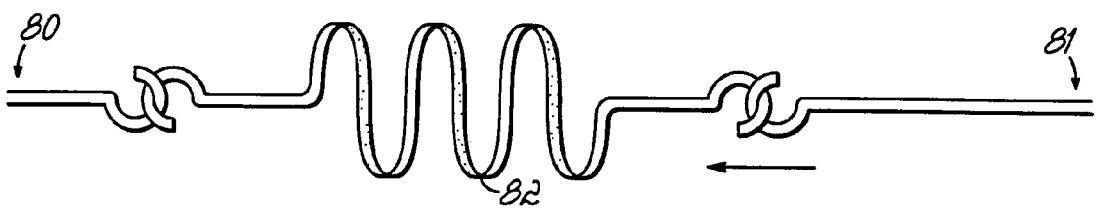

FIG. 25: A tension spring for storing translational energy in 3 sequential stages of its cycle. This may be located at any point between generation of energy (such as a motor, a solenoid, a skeletal muscle harnessing de vice, or other) and delivery to a heart-wall actuator. For one nonlimiting example, it may be within a housing of an electromechanical conversion system, situated between a solenoid or motor and a housing-traversing sliding shaft. 25a shows such a spring [82] at rest. 25b shows it very early after the input end [80] has been retracted by the power source. However, due to the sum of mechanical impedance on the output end [81] (due to the inertia of mechanical parts, heart tissue, and blood, friction, and so forth) the output end has moved negligibly, causing at least part of the mechanical energy imposed by the power source to be stored in the spring due to its elongation. This elongation causes a tensile force to be exerted any conduit or tether attached at the output end, approximately equal to the product of the amount of elongation and the spring constant. This sustained force then effects movement of the attached tension member, dissipating the stored energy at a rate determined by the quantity of force and the impedance transferred through the tension member. Because at least some contributing components of that impedance are time-related (for example, inertia of blood in a heart chamber and viscous deformation of heart tissue), energy delivery occurs over a finite time. 25c shows the spring at the completion of energy delivery. This will be followed by a repositioning of the energy source and a resumption of the configuration of 25a.

Figure 26A:
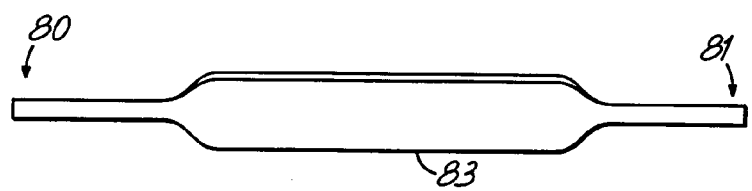
FIG. 26 is a torsion spring for storing rotational energy, also in 3 stages.
Figure 26B:
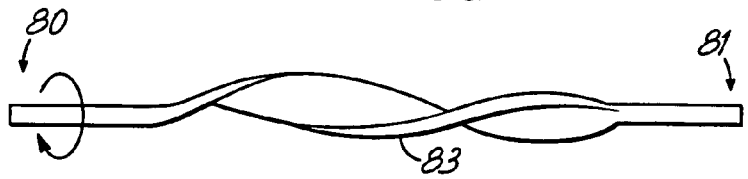
Figure 26C:
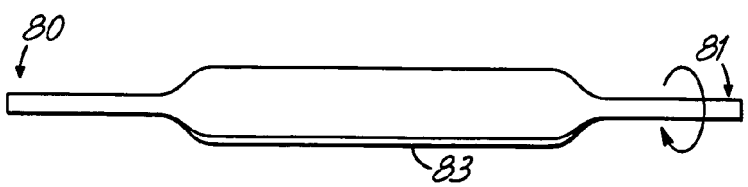

FIG. 26: A torsion spring [83] for storing rotational energy, also in 3 stages. 26a, 26b, and 26c show a torsion spring at rest, having had energy delivered from a power source, connecting to an input end [80], and having delivered that energy over a finite time to a flexible shaft or other conduit of rotary energy, connected to an output end [81], respectively. The physics are completely analogous to those described for the tensile spring in FIG. 26 a, b, and c—with rotation instead of linear displacement and torque instead of force.

Figure 27A:
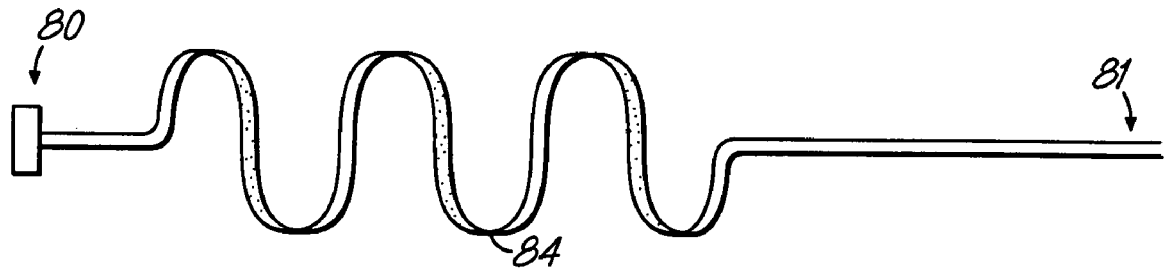
FIG. 27 is a compression spring for storing translational energy, also in 3 stages.
Figure 27B:
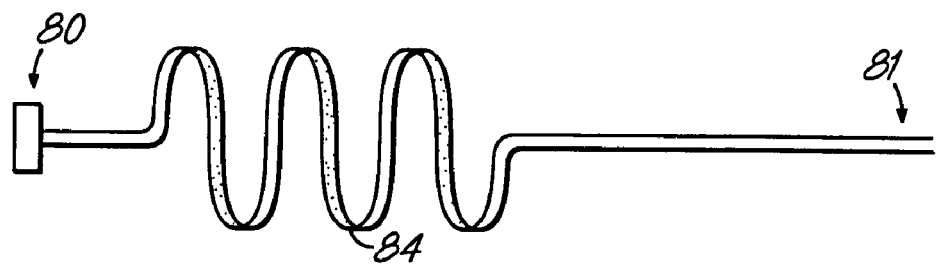
Figure 27C:
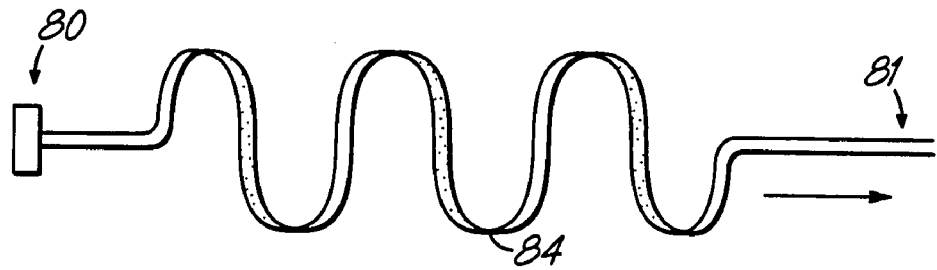

FIG. 27: In an alternative embodiment, it is readily apparent that a strictly analogous transfer and storage of energy occurs with a compression spring similarly situated between source of a compressive force and linear displacement connecting to an input end [80] and a conduit, connected to an output end [81] through which that compressive force and displacement are delivered. These are illustrated in FIGS. 27a, 27b, and 27c.

ii. multiple sequentially activated solenoids. This is already described above under the review of mechanisms for transfer energy out of the power supply housing as FIGS. 23 and 24.

B. Skeletal Muscle Harnessing Mechanisms.

Any of the mechanisms taught in U.S. Pat. No. 6,214,047 may be applied to this use. Specifically:

1. A driver system may comprise, rather than an electromechanical converter, at least one remotely harnessed skeletal muscle linked to a rotary or traction power conduit to an active jacket actuator
2. The skeletal muscle driver system may be configured in such a way that the linkage contains elements to combine the contractile energy of more than one muscle to power a single imposed cardiac ejection.
3. The skeletal muscle driver system may be configured in such a way that the linkage contains elements allowing more than one muscle or group of muscles to power successive imposed cardiac ejections in an alternating manner Control Systems: Mechanisms and Algorithms Control Systems have been designed, with mechanisms and algorithms needed for the active jacket type of heart wall actuator.

Control systems consist of electronic circuitry, which establishes the either the frequency and the pattern of power delivery by an electromechanical or other converter or a skeletal muscle driver system, or the way that frequency and pattern respond to sensed physiologic events.

The controller may be configured so that
a. each actuation is triggered by a detected depolarization of the natural heart, either of the atrium ('p' wave) or of the ventricle ('R' wave)
b. each actuation is triggered by the degree of filling of one or both ventricles, as detected by a sensor or sensors [for example, triggered at a certain volume or ventricular diameter]
c. each actuation is triggered by the rate or relative rate of filling of one or both ventricles [for example, triggered to actuate when the rate of refilling, or dV/dt, as detected by a sensor or sensors, either falls to a set rate or to a set percentage of the maximum rate—and thus indicates that the bulk of filling volume has been achieved]

The controller may be configured so that it is programmable by external signals, whether mediated by radio, microwave, infrared, sonic, mechanical or other means. That programming may adjust
a. the mode of operation (fixed rate and pattern vs. EKG-triggered vs. fill volume vs. fill-rate),
b. the parameters of action in fixed rate mode (the rate as well as velocity and/or other descriptors of actuation pattern),
c. the parameters of action in EKG triggered mode
i. whether p-wave triggered, R-wave triggered, or a conditional response to one or the other
ii. delay, if any, after the triggering signal
iii. conditions in which it returns to a default fixed rate mode, and
iv. sensitivity of triggering [i.e., amplitude of current or voltage necessarily received in order to respond],
d. velocity and/or other descriptors of actuation pattern, whether those descriptors are influenced by a change in rate and/or physiologic signals, and if so, how.
e. the parameters of action in the fill-volume mode (the volume at which actuation is triggered as well as velocity and/or other descriptors of actuation pattern)
f. the parameters of action in the fill-rate mode (whether triggering event is a given filling rate and if so what rate, or whether the triggering event is a slowing to a given percentage of maximum detected filling rate for that stroke and if so what percentage, as well as velocity and/or other descriptors of actuation pattern)

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of applicant's general inventive concept.

What is claimed is:

1. A power system for assisting in the operation of the natural heart, comprising:
   an actuator mechanism for deforming the natural heart;
   a power source for generating translational motion;
   a conduit structure for delivering the motion of the power source to the actuator mechanism, the conduit structure including a conduit and a tether movable in the conduit, the conduit and tether operably coupled between the actuator mechanism and the power source so that translational movement of the conduit and tether with respect to each other actuates the actuator mechanism to effect a deformation of the heart;
   the conduit having apertures formed therein to provide for the passage of tissue fluid into and out of the conduit.

2. The system of claim 1 wherein the conduit is compressible.

3. The system of claim 1 wherein the conduit is in the form of a coil that is compressible.

4. The system of claim 1 wherein the conduit is rigid.

5. The system of claim 1 further comprising a plurality of bearings positioned between the conduit and the tether, the bearings reducing the friction in the movement of the tether in the conduit.

6. The system of claim 5 wherein the bearings are cylindrical and are positioned end to end.

7. The system of claim 6 wherein the cylindrical bearings include radial projections, which engage the conduit and generally prevent translational movement of the bearings in the conduit.

8. The system of claim 6 wherein adjacent bearings have corresponding projection and slots, the projection of one bearing engaging the slot of an adjacent bearing to prevent relative rotation of the adjacent bearings.

9. The system of claim 1 wherein the conduit includes a plurality of beads stacked together to form the conduit, the tether moving in aligned openings in the beads.

10. The system of claim 9 further comprising a jacket surrounding the beads.

11. The system of claim 9 further comprising adhesive positioned between adjacent beads to hold the beads together to form the conduit.

12. The system of claim 9 wherein the beads are thicker on one side than on the other to affect the alignment of the plurality of beads in forming the conduit.

13. The system of claim 9 wherein the at least one of the beads is in the form of a ring.

14. The system of claim 13 wherein the ring includes at least one of an interruption or groove therein.

15. The system of claim 9 wherein the beads are formed of a material from the group including a ceramic, a hard polymer or a hard composite.

16. The system of claim 9 further comprising a spring between at least two adjacent beads.

17. A power system for assisting in the operation of the natural heart, comprising:
    an actuator mechanism for deforming the natural heart, the actuator mechanism including a plurality of blocks;
    a power source for generating rotational motion;
    a conduit structure for delivering the motion of the power source to the actuator mechanism, the conduit structure including a conduit that imparts a rotational motion at a driven end when the conduit is rotated at a driving end, the conduit operably coupled between the actuator mechanism and the power source and coupled to at least one of the blocks so that rotational movement of the conduit rotates the block and actuates the actuator mechanism to effect a deformation of the heart.

18. The system of claim 17 wherein the conduit includes a flexible helix.

19. The system of claim 17 wherein the conduit includes multiple flexible helices.

20. The system of claim 17 wherein the conduit includes a plurality of links, the links being rotationally coupled together with adjacent links.

21. The system of claim 17 wherein the conduit is coupled to a solenoid equipped socket and the block is coupled to a magnetized hub, rotation of the socket causing rotation of the hub and block.

22. A power system for assisting in the operation of the natural heart, comprising:
    an actuator mechanism for deforming the natural heart;
    a power source for generating rotational motion, the power source including a solenoid and a permanent magnet, activation of the solenoid effecting rotational motion;
    a conduit structure for delivering the motion of the power source to the actuator mechanism, the conduit structure including a conduit operably coupled between the actuator mechanism and the power source wherein one of the solenoid and permanent magnet is coupled to the conduit so that the conduit imparts rotational motion at a driven end when the conduit is rotated at a driving end and the rotational motion of the conduit actuates the actuator mechanism to effect a deformation of the heart.

* * * * *